United States Patent

Akong et al.

[11] Patent Number: 6,057,114
[45] Date of Patent: *May 2, 2000

[54] AUTOMATED ASSAYS AND METHODS FOR DETECTING AND MODULATING CELL SURFACE PROTEIN FUNCTION

[75] Inventors: Michael Anthony Akong, San Diego; Michael Miller Harpold, El Cajon; Gonul Velicelebi; Paul Brust, both of San Diego, all of Calif.

[73] Assignee: Sibia Neurosciences, Inc., La Jolla, Calif.

[*] Notice: This patent is subject to a terminal disclaimer.

[21] Appl. No.: 08/434,511

[22] Filed: May 4, 1995

Related U.S. Application Data

[60] Division of application No. 08/244,985, Jun. 20, 1994, Pat. No. 5,670,113, which is a continuation-in-part of application No. 07/812,254, Dec. 20, 1991, abandoned.

[51] Int. Cl.⁷ ................................................. G01N 33/533
[52] U.S. Cl. ............................. 435/7.21; 422/50; 422/55; 422/62; 422/67; 422/68.1; 422/82.03; 422/82.07; 422/82.08; 435/7.2; 435/40.5; 435/40.51; 435/40.52; 436/519; 436/43; 436/800; 436/807; 436/809
[58] Field of Search .................................. 422/50, 55, 62, 422/67, 68.1, 82.03, 82.07, 82.08; 435/7.2, 7.21, 40.5, 40.51, 40.52; 436/519, 43, 800, 807, 809

[56] References Cited

U.S. PATENT DOCUMENTS

| | | | |
|---|---|---|---|
| 3,772,154 | 11/1973 | Isenberg et al. | 195/103.5 R |
| 4,234,540 | 11/1980 | Grinsberg et al. | 422/64 |
| 4,681,742 | 7/1987 | Johnson et al. | 422/102 |
| 4,908,186 | 3/1990 | Sakamaki | 422/64 |
| 5,096,807 | 3/1992 | Leaback | 435/6 |
| 5,104,621 | 4/1992 | Pfost et al. | 422/67 |
| 5,108,703 | 4/1992 | Pfost et al. | 422/65 |
| 5,125,748 | 6/1992 | Bjornson et al. | 356/414 |
| 5,355,215 | 10/1994 | Schroeder et al. | 356/317 |
| 5,386,025 | 1/1995 | Jay et al. | 536/23.5 |
| 5,407,820 | 4/1995 | Ellis et al. | 435/240.2 |

FOREIGN PATENT DOCUMENTS

| | | |
|---|---|---|
| 0266881 | 6/1988 | European Pat. Off. . |
| 0355738 | 2/1990 | European Pat. Off. . |
| 0441755 | 8/1991 | European Pat. Off. . |
| 0355738 | 11/1994 | European Pat. Off. . |
| 60-040955 | 3/1985 | Japan . |
| 02059647 | 2/1990 | Japan . |
| 03085455 | 4/1991 | Japan . |
| 8909834 | 10/1989 | WIPO . |
| 9115602 | 11/1991 | WIPO . |
| 9202639 | 2/1992 | WIPO . |
| 9219772 | 11/1994 | WIPO . |
| 9605488 | 2/1996 | WIPO | G01J 3/30 |

OTHER PUBLICATIONS

Database WPI, Derwent Abstract of Japanese Patent 60–40955, published Mar. 4, 1985.
Database WPI, Derwent Abstract of Japanese Patent 2–59647, published Feb. 28, 1990.
Database WPI, Derwent Abstract of Japanese Patent 3–85455, published Apr. 10, 1991.

(List continued on next page.)

*Primary Examiner*—James C. Housel
*Assistant Examiner*—Bao-Thuy L. Nguyen
*Attorney, Agent, or Firm*—Stephanie L. Seidman; Heller Ehrman White & McAuliffe

[57] ABSTRACT

Automated assays for detecting and measuring ion channel and cell surface receptor activity and for identifying compounds that modulate or potentiate such activity are provided. Among the assays are fluorescent indicator-based assays that use cells containing effective levels of a fluorescent indicator that is responsive to changes in ion concentration. Activation of the ion channels or receptors is initiated in the automated measurement apparatus by injection into one or more predetermined cell-containing wells of a reagent which is a known or possible activator or inhibitor of the ion channels or receptors of interest. The resulting activity of the ion channels or receptors, which causes changes in ion concentration in the cytoplasm, is determined by measurement of fluorescence intensity changes of the indicator in response to an excitation wavelength.

62 Claims, 14 Drawing Sheets

OTHER PUBLICATIONS

Summarized Translation (from Japanese foreign associate) of Japanese Patent 60–40955, published Mar. 4, 1985.

Summarized Translation (from Japanese foreign associate) of Japanese Patent 2–59647, published Feb. 28, 1990.

Summarized Translation (from Japanese foreign associate) of Japanese Patent 3–85455, published Apr. 10, 1991.

English translation of Japanese Patent 60–40955, published Mar. 4, 1995.

English translation of Japanese Patent 3–85455, published Apr. 10, 1991.

Brooker, et al., "Calcium wave evoked by activation of endogenous or exogenously expressed receptors in Xenopus oocytes," *Proc. Natl. Acad. Sci USA*, 87:2813–2817 (1990).

Bujo, et al., "Different sensitivities to agonist of muscarinic acetylcholine receptor subtypes," *FEBS LTTRS.* 240:95–100 (1988).

Cornell–Bell, et al., "Glutamate induces calcium waves in cultured astrocytes: long–range glial signalling," *Science*, 247:470–473 (1990).

Flow Laboratories "Fluoroskan II, Operating Instructions" (1988).

Gutierrez, et al., "Dihydropyridine–sensitive calcium channels from skeletal muscle," *J. of Biol. Chem.*, 266(25):16387–16394 (1991).

ICN Biomedicals, Inc., "DIGIFLEX–TP™ Automatic Pipette (Model 33020), Operating and Service Manual" (1986).

Jensen, et al., "Fluorescence measurement of changes in intracellular calcium induced by excitatory amino acids culture cortical astrocytes," *J. of Neuroscience*, 10(4):1165–1175 (1990).

Kao, et al., "Photochemically generated cytosolic calcium pulses and their detection by Fluo–3," *J. Biol. Chem.*, 264(14):8179–8184 (1989).

Meyer, et al., "Kinetics of calcium channel opening by inositol 1,4,5–Triphosphate," *Biochemistry*, 29:32–37 (1990).

Miller, "the revenge of the kainate receptor," *TINS*, 14(11):447–479 (1991).

Minta, et al., "Fluorescent indicators for cytosolic calcium based on rhodamine and fluorescein chromophores," *J. Biol. Chem.*, 264(14):8171–8178 (1989).

Rijkers, et al. "Improved Method for Measuring Intracellular $Ca^{++}$ with Fluo–3" *Cytometry 11*:923–927 (1990).

van den Pol, et al. "Glutamate, the Dominant–Excitatory transmitter in Neuroendocrine Regulation" *Science 250*:1276–1278 (1990).

Wall, et al. "Rapid Functional Assay for Multidrug Resistance in Human Tumor cell Lines using the Fluorescent Indictaro Fluo–3," *J. Natl.Cancer Inst. 83*:206–207 (1991).

Williams, et al. "Structure and Functional Expression of an ω–Conotoxin–Sensitive Human N–Type Calcium Channel," *Science 257*:389–39 (1992).

Williams, et al., "Structure and functional expression of $\alpha_1$, $\alpha_2$ and $\beta$ subunits of a novel human neuronal calcium channel subtype," *Neuron*, 8:71–84 (1992).

| | |
|---|---|
| START WELL | 3, 3 |
| NUMBER OF WELLS | 8 |
| REAGENT QUANTITY DRAW | 50 μl |
| REAGENT QUANTITY PUMP | 50 μl |
| EXCITATION FILTER | ex2 |
| EMISSION FILTER | em2 |
| PRE-REAGENT READS | 5 |
| POST-REAGENT READS | 125 |
| DATA FILE NAME | TEST1 |
| SYRINGE SPEED | W2 |

*Fig. 7*

| | |
|---|---|
| START COLUMN | 1 |
| NUMBER OF COLUMNS | 12 |
| REAGENT QUANTITY | 50 μl |
| EXCITATION FILTER | ex2 |
| EMISSION FILTER | em2 |
| PRE-REAGENT READS | 5 |
| POST-REAGENT READS | 125 |
| DATA FILE NAME | TEST II |

AUTOMATED ASSAYS AND METHODS FOR DETECTING AND MODULATING CELL SURFACE PROTEIN FUNCTION

This application is a divisional of U.S. application Ser. No. 08/244,985, filed Jun. 20, 1994, now U.S. Pat. No. 5,670,113, which is a continuation-in-part of U.S. application Ser. No. 07/812,254, filed Dec. 20, 1991, now abandoned.

BACKGROUND OF THE INVENTION

This invention relates to methods and apparatus for assaying biological samples to which a reagent is added and particularly, to computer-controlled methods and apparatus for such assaying.

Assaying processes are well known in which a reagent is added to a sample, and measurements of the sample and reagent are made to identify sample attributes stimulated by the reagent. For example, one such assay process concerns determining in a chromogenic assay the amount of an enzyme present in a biological sample or solution. Such assays are based on the development of a colored product in the reaction solution. The reaction develops as the enzyme catalyzes the conversion of a colorless chromogenic substrate to a colored product.

In such assays it is often required to determine the enzymatic activity of a number of samples and at one or more dilutions. Enzymatic reactions characteristically proceed at a constant rate provided substrate is present in a large molar excess, i.e., the concentration of substrate does not limit the rate of reaction. With such kinetic parameters, it may be convenient to set up several reaction solutions separately in the wells of a microtiter plate, for example, carrying out each reaction for a predetermined constant amount of time and stopping the reactions while they are still in a linear range of the assay. With each of the so-called end-point reactions stopped, no further color development occurs and the reaction solutions in the separate wells of the microtiter may be read at any convenient time.

Plate readers which automatically read the intensity of a colored solution in an array of wells are known. Also, plate readers which measure the amount of fluorescence in a well of a microtiter plate are known.

Classically, assays of the above-described type are performed by a laboratory worker who prepares the sample, manually adds a precise amount of reagent to the sample, and then measures the result at one or more preselected times after the reagent addition. This classical approach is very time consuming for the laboratory worker and additionally, when the stimulated reaction yields time-varying results, precise timing on the part of the laboratory worker is required. If such timing is not properly performed, erroneous assay results may occur.

One known laboratory device for partially automating tests to detect fluorescence as a measurable attribute is the Fluoroskan II. The Fluoroskan II includes a plate carrier system to hold a sample-containing plate having a plurality, e.g., 96, of sample-containing wells. A laboratory worker places a portion of the sample into some or all of the wells of the plate, and then adds reagent to the sample-containing wells. The plate is then placed in the Fluoroskan II which automatically measures the fluorescence of the samples in the wells. Although this known apparatus has proven valuable for fluorescence testing, some problems, which were also inherent in the classical testing, still remain. For example, the addition of reagent by the laboratory worker still requires a large amount of laboratory work time. Also, since the measured results of reactions may be dependent on the time elapsed since reagent addition, the first samples to receive reagent may have progressed past the point of meaningful reaction results by the time all samples have received reagent. Further, some reactions complete so quickly that it is nearly impossible to add reagent to a sample, move the sample plate to the assay apparatus and move the sample to a measurement position before the reaction has run to completion.

A need exists to rapidly screen compounds to determine their effect on a protein's function such as cell surface proteins like ion channels and receptors, the regulation of which surface proteins can be important in treating certain disease states. Such cell surface proteins permit intracellular transduction of extracellular signals. These cell surface proteins, by transmitting information regarding extracellular stimuli via specific intracellular pathways, induce an appropriate cellular response to external stimuli. The response may be immediate and transient, slow and sustained, or some mixture thereof. By virtue of an array of varied membrane surface proteins, normal (i.e., non-diseased) cells and tissue are exquisitely sensitive to their environment. Compounds which are capable of potentiating or inhibiting activation of voltage-dependent calcium channels are believed to be useful in treating a variety of diseases including certain cardiovascular and nervous system disorders. Similarly, compounds which can affect the functioning of cell surface receptors may be beneficial in the treatment of certain other diseases. Thus, it is desirable to identify compounds capable of activating, potentiating or inhibiting such cell surface proteins using functional assays. Such assays require study of the kinetics of the reaction in real time due to their transient nature. Heretofore, such assays have required a substantial amount of time from highly skilled researchers and technicians to conduct and record the results of individual assays. Also, with respect to functional assays for cell surface proteins which utilize electrophysiological or fluorescence imaging techniques, laboratory equipment which is required is often extremely costly.

A need also exists for an automated analysis apparatus which is capable of automatically adding reagent to contained samples and measuring reaction results to minimize lab worker time requirements, and to provide accurate measurement of time varying reactions. It would also be very advantageous, inasmuch as drug companies now typically screen thousands to tens of thousands of compounds in the hope of finding a desired activity, to be able to provide a rapid automated method for assaying a compound or a series of compounds for ability to affect cell surface proteins, such as ion channels and receptors or cytoplasmic receptors, where a plurality of tests may be conducted seriatim and the results recorded with no, or only occasional, intervention by the researcher.

SUMMARY OF THE INVENTION

This need is met and a technical advance is achieved with the present invention, which in one aspect is a computer-controlled measurement apparatus for automatically adding reagent to a predetermined sample-containing wells and measuring at least one attribute of the samples in the predetermined wells. The computer-controlled measurement apparatus comprises a plate having a plurality of solution-containing wells, reagent-adding equipment responsive to the computer for adding reagent to the wells, measurement equipment for measuring at least one attribute, e.g., fluorescence, of the solution contained by the wells and moving equipment which is responsive to the computer for aligning the wells with the reagent-adding component and with the fluorescence measurement device.

The computer exercises control over the operation of the various components involved in order to properly coordinate the main functions of the apparatus: reagent addition and attribute measurement. The computer issues several types of commands to provide the necessary coordination. In one embodiment, alignment of wells with reagent-adding and fluorescence-measuring devices is accomplished by computer-issued plate movement commands which are sent to the plate-moving equipment which responds by moving predetermined wells to the reagent-adding position, then to the measurement position. Pump commands are generated by the computer to direct the reagent-adding equipment to add a predetermined volume of the reagent to the predetermined wells at the reagent-adding position. Additionally, measurement commands are generated by the computer to direct the measuring equipment to measure a plurality of fluorescence magnitude values of the samples in the predetermined wells. The values determined by the measurement equipment are recorded within the assay apparatus for later use. In the preferred embodiment, the measured values are first stored within a microcomputer, which comprises the controller, and later moved to a disk drive for long-term storage. The microcomputer may be further equipped with data analysis programs that transform the data into relevant statistics and/or display the data in various formats.

In accordance with one embodiment of the present invention, regarding the performance of the present assay, the controller first aligns a predetermined well containing a sample to be assayed with; the fluid outlet of the reagent-adding equipment, then controls the reagent-adding equipment to add a predetermined volume of reagent to the predetermined well. After reagent is added, the predetermined well is aligned, under the control of the controller, with the measurement equipment. The fluorescence of the sample in the predetermined well is measured using a filter and a photomultiplier tube or photodiode array or a charge coupled device (CCD) to detect emitted light, again in response to computer control, while the predetermined well is aligned with the measurement position. Advantageously, the measurement equipment may comprise a light source and filters for stimulating fluorescence and a photomultiplier tube (or photodiode array or CCD) to detect light emitted by the sample in the predetermined well using fiber optic cables to send and receive light.

In certain situations, the sample contained by a well may exhibit background levels of the attribute to be measured, e.g., fluorescence, even before reagent is added to the well. In such cases, it is desirable to measure the attribute prior to adding reagent so that background (pre-reagent) values can be used in data analysis to more accurately evaluate the measured post-reagent values. Accordingly, for certain tests the predetermined well is aligned, under the control of the controller, with the measuring equipment, and pre-reagent measurements are taken and stored.

A method of operation of a computer-controlled fluorescence-measuring apparatus comprises identifying a predetermined well to be measured, moving the predetermined well to a reagent-adding position, and adding reagent to the predetermined well while at the reagent-adding position. After adding reagent, the predetermined well is moved to a measurement position where the fluorescence of the sample in the predetermined well is measured and the data from such measurement recorded. In certain situations, the pre-reagent fluorescence of the sample in the predetermined well may be measured by moving the predetermined well to the measuring position and measuring fluorescence values prior to the adding of reagent.

In a particularly preferred embodiment of the present invention, one or more wells, preferably a plurality of wells arranged in a predetermined array (e.g., a column of 8 wells), are assayed without having to move the plate for addition of reagent once the well or wells to be assayed have been positioned at the reagent-adding/detecting position. Alignment of wells with reagent-adding and fluorescence-measuring devices is accomplished by computer-issued plate movement equipment which responds by moving predetermined wells to such an assay position at which reagent addition and fluorescence measurement both occur. After the assay of the predetermined well(s), other wells may be moved into the assay position, and the method repeated. In such a preferred embodiment, the apparatus may be configured such that fluorescence measurements may desirably be taken from beneath (i.e., through the bottom of) the wells, thus permitting continuous fluorescence measurement before, during and after reagent is pumped into the wells from above.

A further preferred embodiment of the apparatus of the invention employs a computer-controlled robotic arm device to move the position of the fluid outlet(s) of the reagent-adding device between the reagent-adding/detecting position and one or more predetermined positions to pick up aliquots of reagent or buffer for delivery to the wells at the reagent-adding/measurement position or to dispose of spent liquid from, e.g., the wells. This embodiment of the invention provides for the delivery of aliquots of reagent without the need to prime the reagent-adding device with relatively large volumes. Very importantly, employing a computer-controlled robotic arm device to move the reagent-adding device provides the capability of testing several different reagents at the same time, individually delivering a specific reagent to a specific well, and/or sequentially delivering more than one reagent to one or more assay wells. Particularly where the reagent-adding/measurement position accommodates a plurality of wells, a variety of reagents may be added to wells singly, or in duplicate, triplicate, etc.

Further, because the reagent-adding device is capable of picking-up as well as delivering fluid, and because it may be moved under computer control in the x, y, and z axes, in this embodiment of the invention the sample-containing wells may be washed immediately prior to being assayed by automatically aspirating buffer from the assay wells, moving to a discard location and discarding the spent buffer solution, moving to a location having a reservoir of fresh buffer and picking-up an aliquot of the buffer and delivering it to the assay wells (and optionally repeating these steps one or more times) before moving to a location to pick-up an aliquot of reagent and returning to the reagent-adding/detecting position to initiate the assay. In fluorescent indicator-based cell assays as described herein, such a washing function may be desirable for removing excess fluorescent indicator which was not incorporated into the cells during loading. Also, by automatically pipetting and discarding buffer, the fluid outlets of the reagent-adding device may be washed between deliveries of different reagents. Similarly, the use of the robotically-controlled reagent-adding device provides for sequential delivery of more than one reagent to any one or more wells being assayed while fluorescence measurements are being taken.

In another embodiment of the present invention, an automated method is provided for testing the response of a cell having receptors or membrane-spanning ion channels to one or more compounds having putative ion channel or receptor modulatory activity, where the ion channels or receptors of the cells, when activated, are capable of directly or indirectly causing a change in the concentration of ions in the cytoplasm, and wherein the degree of activation or inactivation of the ion channels or receptors is determined by a change in fluorescence intensity in the cytoplasm of the cells which cells have been loaded with an amount of an ion-sensitive fluorescent indicator sufficient to detect a change in intracellular ion concentration.

In a particular aspect, the invention provides an automated method for rapid functional screening of compounds to identify potential pharmaceuticals, i.e., drugs. An efficient drug-screening method is provided which utilizes the computer-controlled fluorescence-measuring apparatus described above for rapid automated analysis of one or more compounds that is based on functional evaluation of drug targets, i.e., receptors and ion channels, in their physiological environment, i.e., living cells, in the presence of the potential pharmaceuticals. In the performance of the drug-screening assay, the sample wells contain receptor- and/or ion channel-expressing cells. Where the test compound is a known or putative agonist (a compound that activates the receptor or ion channel) it may be delivered to the wells via the reagent-adding device; where the compound is a known or putative antagonist or a potentiator (that is, an agonist-like compound which augments agonist activity, but cannot itself cause activation, such as the calcium channel potentiator, Bay K8644) the compound may be (1) included in the well(s) before the plate is introduced into the apparatus of the invention, (2) added by the reagent-adding device along with addition of the agonist reagent used to activate the receptors or ion channels, or (3) added by the movable reagent-adding device prior to addition of the agonist (i.e., sequential addition of reagents). Because many cells can be assayed in a relatively short period of time, the present invention enables rapid analysis of replicate samples, including control samples, and provides a possibility for screening multiple compounds and/or multiple doses of compounds in a single operation. Further, because in preferred embodiments, single or sequential additions of compounds can be made without moving the plate, fluorescence changes caused by the addition of a wide variety of known or unknown compounds may be measured, which greatly enhances the ability of the assays to rapidly identify compounds having agonist, antagonist or potentiating activity. In an especially preferred embodiment, the cells are recombinant cells expressing a homogeneous population of recombinant receptors and/or ion channels thereby providing an assay which is valuable for determining the specificity of a compound having putative agonist or antagonist activity with respect to the receptors or ion channels.

BRIEF DESCRIPTION OF THE DRAWINGS

FIG. 7 represents a monitor screen displayed list of test parameters and values assigned thereto;

DETAILED DESCRIPTION OF THE INVENTION

Figure 1:
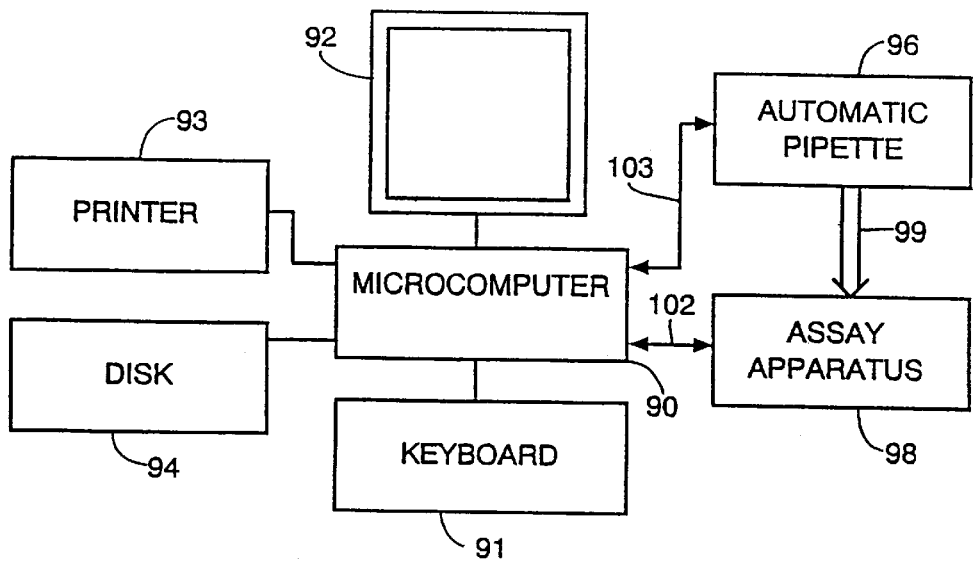
FIG. 1 is a block diagram of an automated apparatus embodying the invention.

FIG. 1 is a block diagram of a system embodying the present invention. The system includes a microcomputer 90 connected in the conventional manner to a keyboard 91, a monitor 92, a printer 93 and a disk drive 94. In the preferred embodiment, microcomputer 90 is an IBM or IBM-compatible microprocessor (e.g., a microcomputer commonly known as an IBM PC). Assays are performed by cooperative interaction of an automatic pipette 96 and an assay apparatus 98, which are controlled by microcomputer 90 via a respective one of bi-directional buses 103 and 102. In the preferred embodiment, communication over buses 102 and 103 is in the RS-232C format. During an assay, automatic pipette 96, at times and in amounts controlled by microcomputer 90, pumps reagent to assay apparatus 98 via tubing 99. The assay apparatus 98 is used to individually measure fluorescence of solutions contained by a plurality of solution wells. Under control of microcomputer 90, the solution in a given well receives the predetermined quantity of reagent from automatic pipette 96 and the fluorescence of the solution in that well is measured by assay apparatus 98 and recorded in the microcomputer 90 for later analysis.

Figure 2:
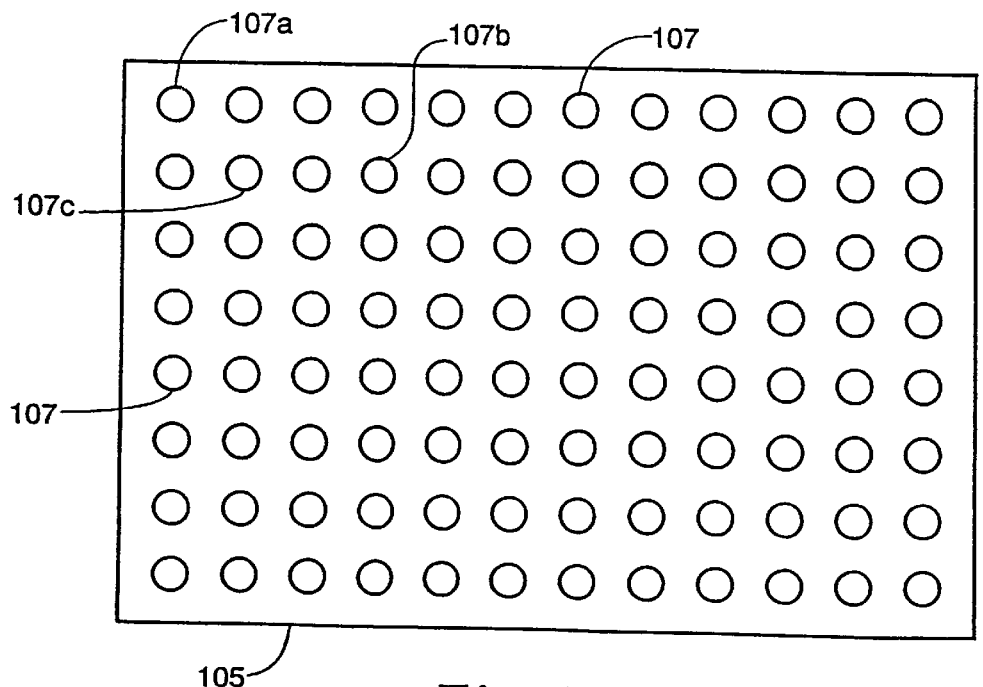
FIG. 2 is a plan view of a multi-well plate used with an assay apparatus of FIG. 1.

The quantities of solution are presented to the assay apparatus 98 for measurement in a multi-well plate 105 as shown in plan view in FIG. 2. Multi-well plate 105 comprises 96 recesses or wells 107, each for receiving an individual quantity of solution for analysis. The wells 107 are regularly spaced to form a rectangular array having eight rows of wells 107 with each row comprising 12 columns of wells. Each well has a specific X,Y location in the array with the variable X denoting one of the 12 columns, and the variable Y denoting one specific well within the column identified by the X variable. For example, the well denoted 107*a* in FIG. 2 is identified as well 1,1, while the well denoted 107*b* is identified by as well 4,2. In preparation for analysis, solutions to be tested are placed in some or all of the wells 107 and the multi-well plate 105 is placed in assay apparatus 98.

Figure 3:
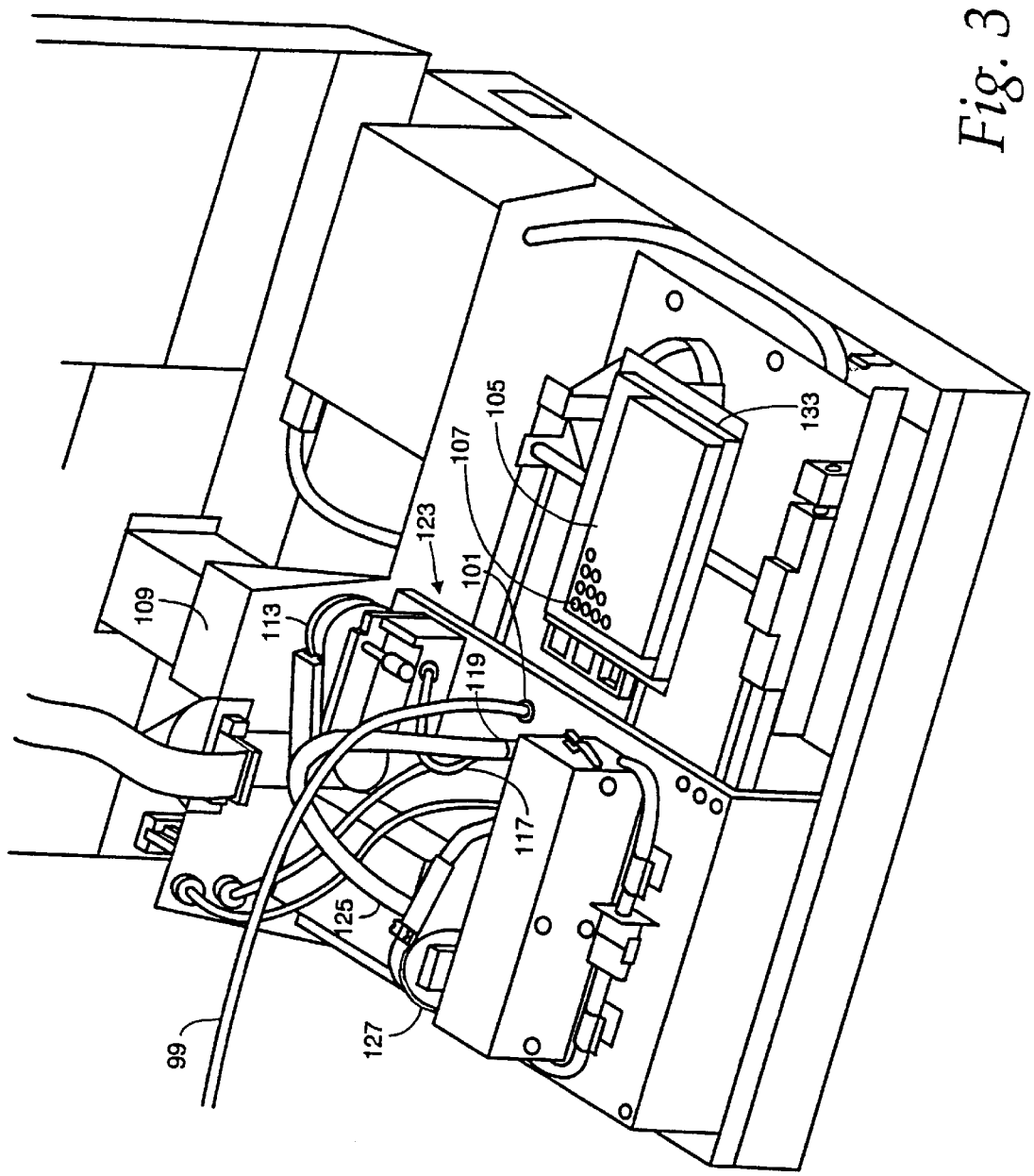
FIG. 3 is a perspective view of the internal structure of the assay apparatus of FIG. 1.

FIG. 3 is a perspective view of the internal components of assay apparatus 98 showing a multi-well plate 105 therein. The assay apparatus 98 in the present embodiment is a modified version of the Fluoroskan II manufactured by Labsystems of Helsinki, Finland (Sold in the United States by Lab Products International, Raleigh, N.C.). The operation of the Fluoroskan II and its interaction with a microcomputer are well known in the art and are described for example in the Fluoroskan II operating instructions No.

1500750. Portions of the assay apparatus 98 shown in FIG. 3 are also shown in a selective diagrammatic perspective view in FIG. 4 for ease of understanding.

Assay apparatus 98, exposes the samples in individual wells 107 to excitation light wave radiation of preprogrammed wavelengths and measures the fluorescence of the samples at preprogrammed emission wavelengths. The fluorescence of the solution in a given well can be measured a number of times and digital values representing each measurement are generated and stored. The excitation light source is a Xenon lamp 109 which generates electromagnetic radiation in the range of 300 to 1,000 nanometers wavelength. Light from lamp 109 is collected by a lens and fiber optic arrangement 111 and conveyed to an excitation fiber optic cable 117 by a software controllable optical filter 113. An optical exciter/sampler 119 which is attached to and extends through a relatively stationary mounting surface 123 (FIG. 3) of assay apparatus 98 receives the light conveyed by optical fiber 117. The light received by optical exciter/ sampler 119 is distributed by a lens 121 to a fixed point of approximately the same area as well 107 beneath mounting surface 123 (FIG. 4) In the present example, the point beneath mounting plate 123 which receives light from lens 121 is called the sample point.

Lens 121 also collects light emitted from a well at the sample point beneath mounting surface 123 and couples the light so collected to a fiber optic cable 125. A software-controllable emission optical filter 127 couples a selected range of wavelengths of the light conveyed by fiber optic cable 125 to a photo-multiplier tube 131 via a fiber optic cable 129. The magnitude of the light conveyed by fiber 129 is converted to an analog electrical signal from which a digital light amplitude representation is periodically generated.

The liquid reagent which is added to wells 107 is provided to assay apparatus 98 in pre-programmed quantities via tube 99. An outlet tip 101 of tube 99 is attached to and extends through mounting surface 123 at a fixed location relative to the attachment of exciter/sampler 119. In the present embodiment, fluid tip 101 and optical exciter/sampler 119 are mounted to surface 123 such that when a well e.g., 107c in a given row, is under the exciter/sampler 119, a well, e.g., 107b, two columns to the right (FIG. 2) in the same row is under fluid tip 101.

Figure 4:
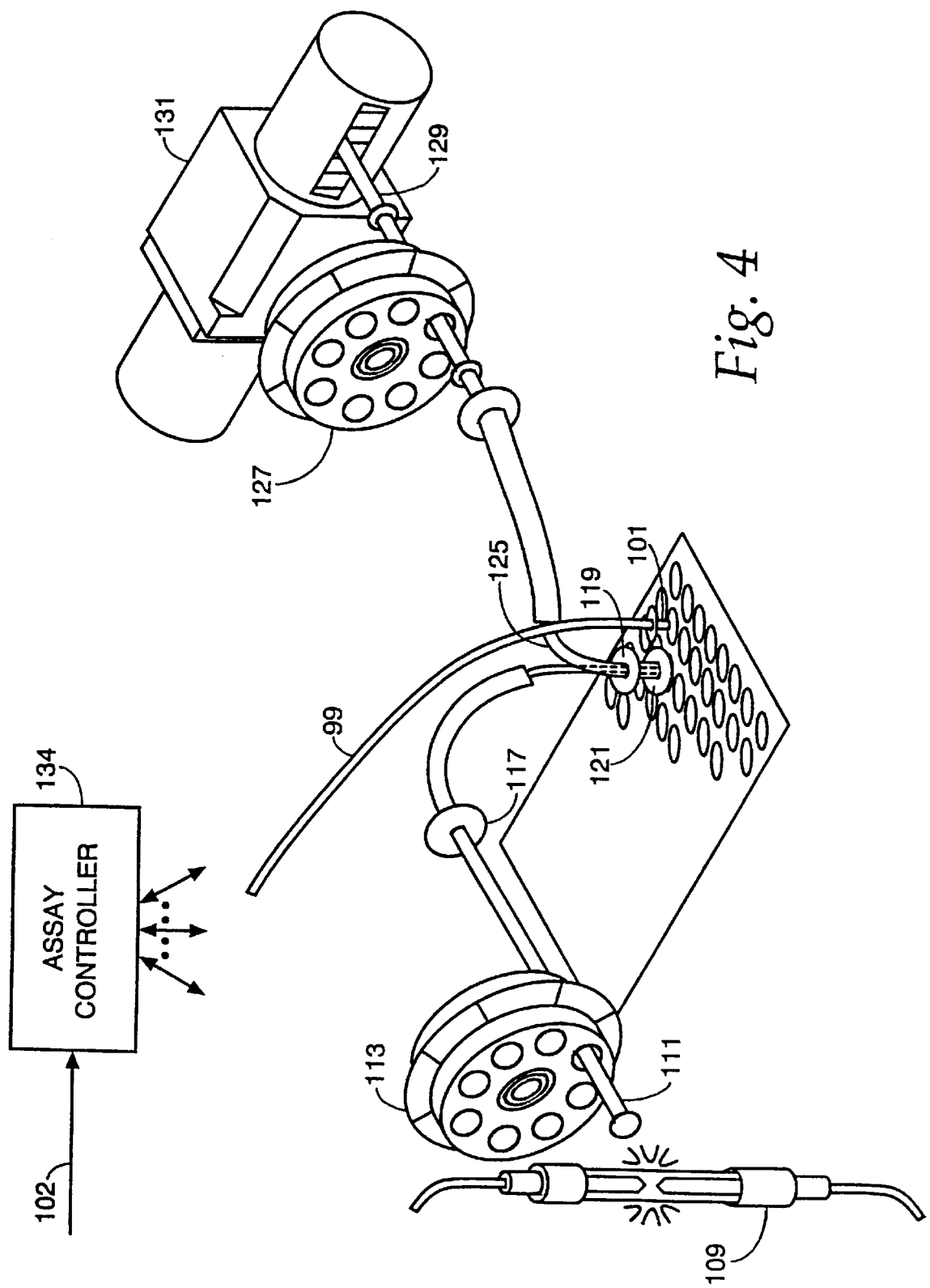
FIG. 4 is a diagrammatic perspective view of the structure of the assay apparatus emphasizing portions thereof.

The multi-well plate 105 is carried in assay apparatus 98 by a plate-carrier system 133 which moves plate 105 in a rectangular coordinate manner to place any of the wells 107 under the exciter/sampler 119 or under the fluid tip 101 responsive to plate movement commands from microcomputer 90 (FIG. 3). Assay apparatus 98 includes an assay controller 134 which is connected to microcomputer 90 by bi-directional bus 102 (FIG. 4). Assay controller 134 operates in a manner disclosed in the Fluoroskan II descriptive material to receive commands from microprocessor 90 and implement functions specified in those commands. Assay controller 134 receives filter set up commands from microcomputer 90 to which it responds by rotating optical filters 113 and 127 to values specified in the filter set up commands. Also, assay controller 134 receives plate movement commands specifying a particular well 107 to move to a position under exciter/sampler 119 or reagent-adding tip 101. Assay controller 134 responds to such plate movement commands by controlling the plate movement system 133 to appropriately position the specified well. In addition, assay controller 134 generates digital representations of fluorescence magnitudes sensed by photo-multiplier tube 131 and returns those digital representations to microcomputer 90.

Automatic pipette 96 of the present embodiment is a modified version of the Digiflex-TP model 33020 manufactured by ICN Biomedicals, Inc. of Horsham, Pa. As is well known in the art and described in the Digiflex-TP operating manual, the automatic pipette 96 is capable of operating under microcomputer control to dispense precise amounts of selected fluids through an outgoing tube, such as tube 99. The Digiflex-TP includes a pair of syringes for dispensing fluids; however, in the present embodiment, only a single syringe 135 (FIG. 5) is used.

Automatic pipette 96 includes a pipette controller 139 which is connected to microcomputer 90 by bus 103 for controlling the functions of the automatic pipette. The specific means for exercising such control are well known from the Digiflex-TP operating manual and are not described in detail herein.

Figure 5:
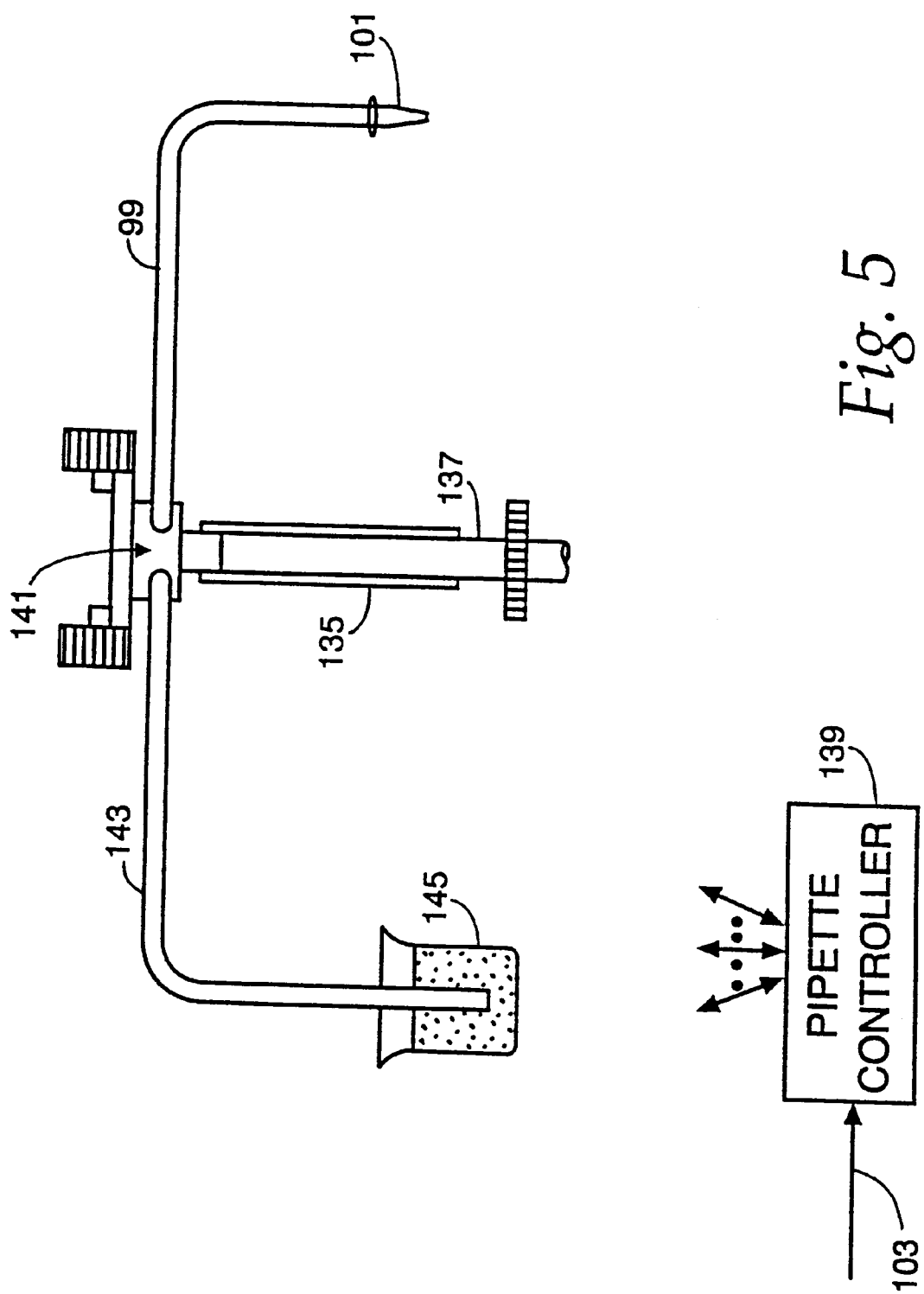
FIG. 5 is a diagrammatic view of the structure of an automatic pipette of the embodiment of FIG. 1.

FIG. 5 shows selected components of automatic pipette 96 which are used in the present embodiment to dispense reagent to assay apparatus 98 via tube 99. Syringe 135 of the automatic pipette 96 includes a plunger 137 for drawing reagent into the syringe 135 and pumping the reagent from the syringe under the control of pipette controller 139. Syringe 135 also includes two-position valve 141 which, under control from pipette controller 139, selectively connects syringe 135 into fluid contact with outgoing tube 99 and with a reagent input tube 143. As previously described, outgoing tube 99 conveys reagent to the wells 107 of multi-well plate 105 in the assay apparatus 98 via a fluid tip 101. Reagent input tubing 143 conveys reagent from a reagent vessel 145 to the syringe 135.

Pipette controller 139 receives set up commands from microcomputer 90 at the beginning of an assay operation. The set up commands pre-establish the amount of reagent to be drawn into syringe 135 responsive to a draw command and the amount of reagent to be pumped from syringe 135 responsive to a pump command. The set up commands also specify the rate at which reagent is to be drawn into the syringe 135 and pumped from the syringe. Three rates W1, W2 and W3, which represent fast, half-fast and one-fourth fast plunger speeds respectively, are available. In the present embodiment W1 is used.

Precisely controlled amounts of reagent can be delivered to assay apparatus 98 by a sequence of valve control and plunger control (draw and pump) commands after pre-establishing the amounts and rates of reagent to be moved by syringe 135. First, a fluid-in command is sent to automatic pipette 96 to connect input tube 143 into fluid communication with syringe 135 via valve 141. A draw command is then sent to automatic pipette 96 to which pipette controller 139 responds by drawing plunger 137 the pre-established amount at the pre-established rate. Microcomputer 90 then transmits a fluid output command to which pipette controller 139 responds by changing the position of valve 141 to connect syringe 135 to output tube 99. When a pump command is received by pipette controller 139, the plunger 137 is pushed into syringe 135 by the pre-established amount at the pre-established rate. Such plunger movement pumps the pre-established amount of reagent from syringe 135 and out of tip 101 into a well 107 of multi-well plate 105.

Figure 6A:
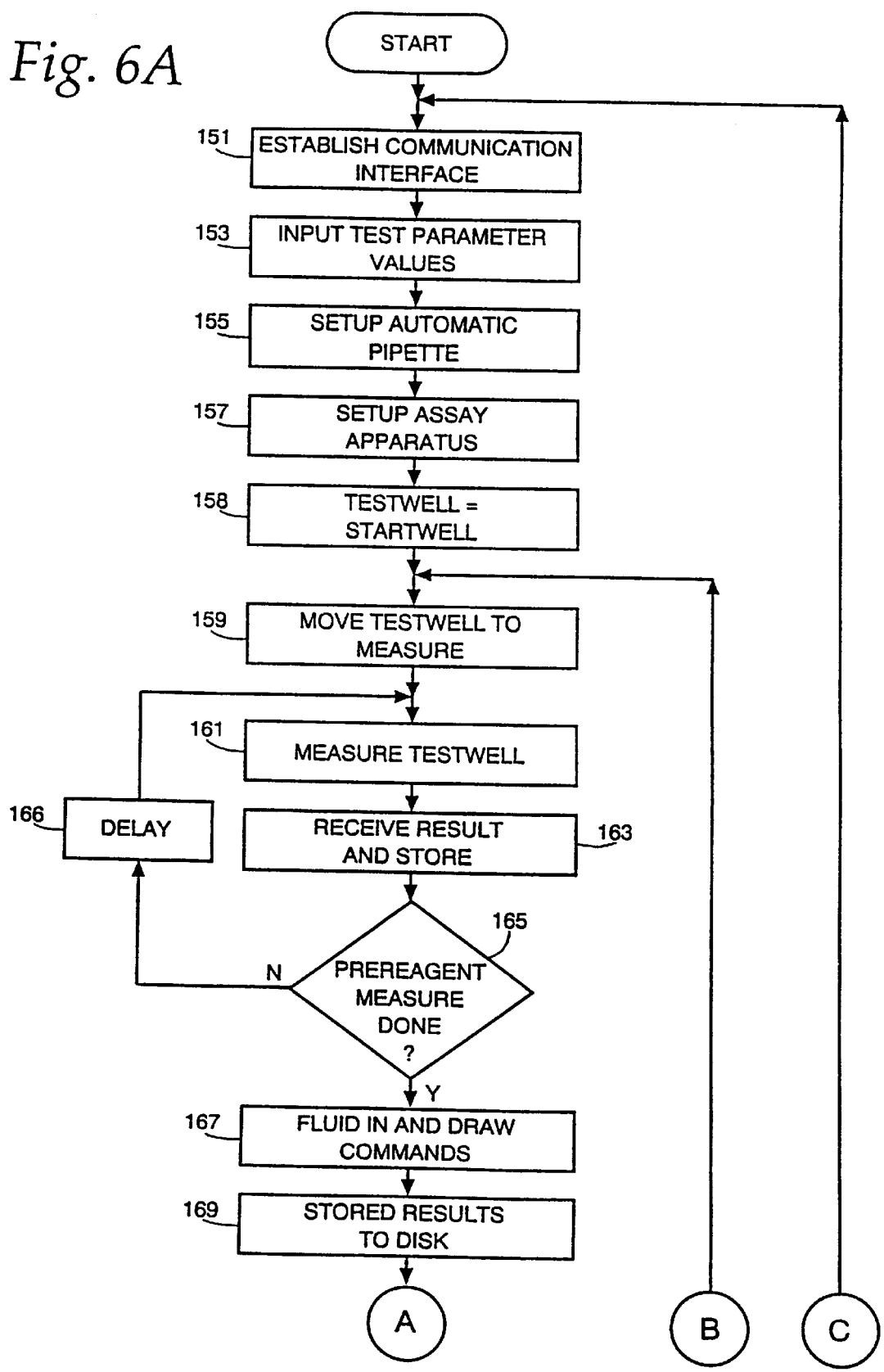
FIG. 6 is a flow diagram of a program implemented by a microcomputer to coordinate the performance of assays by the embodiment of FIG. 1.
Figure 6B:
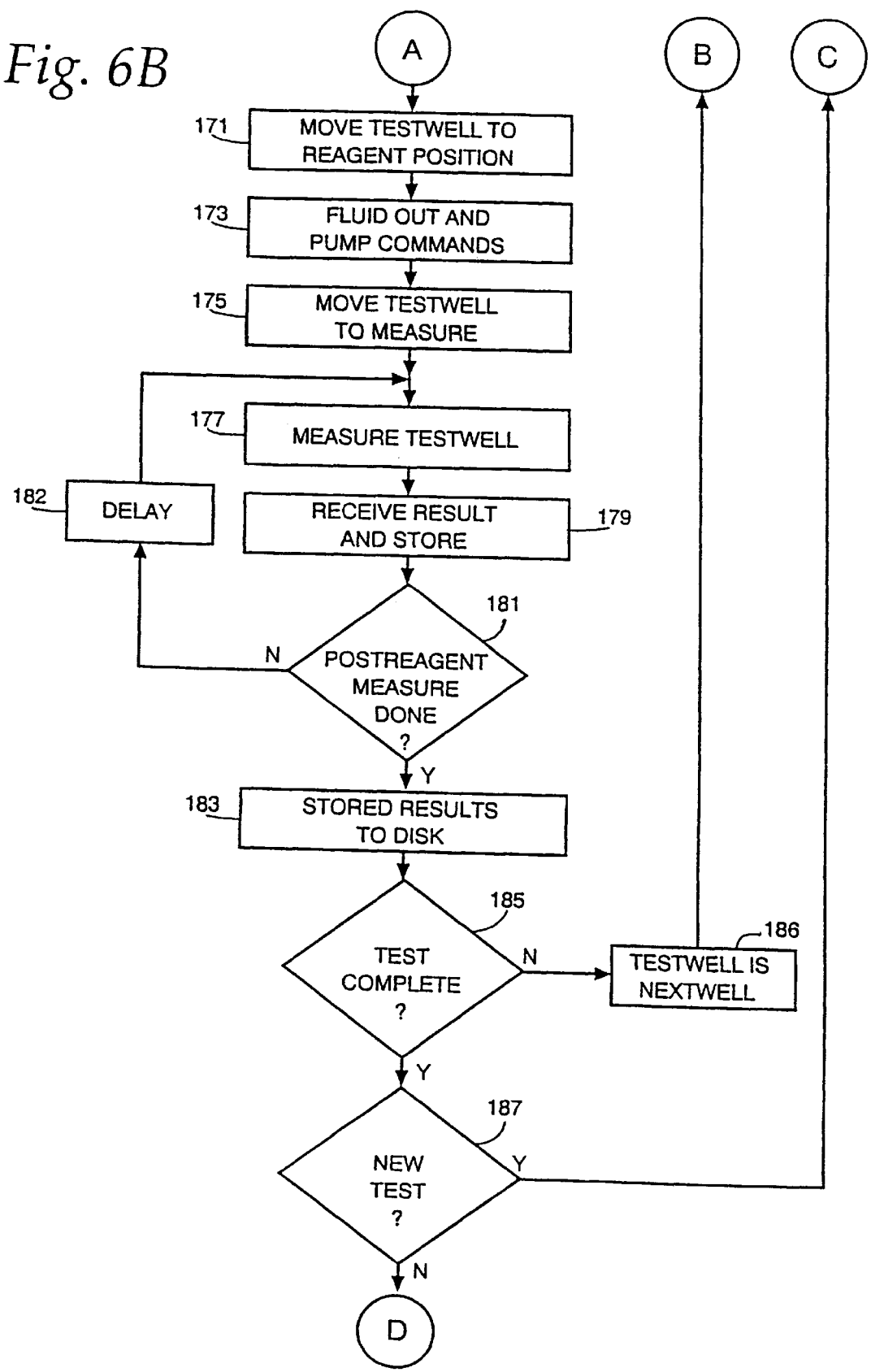
Figure 6C:
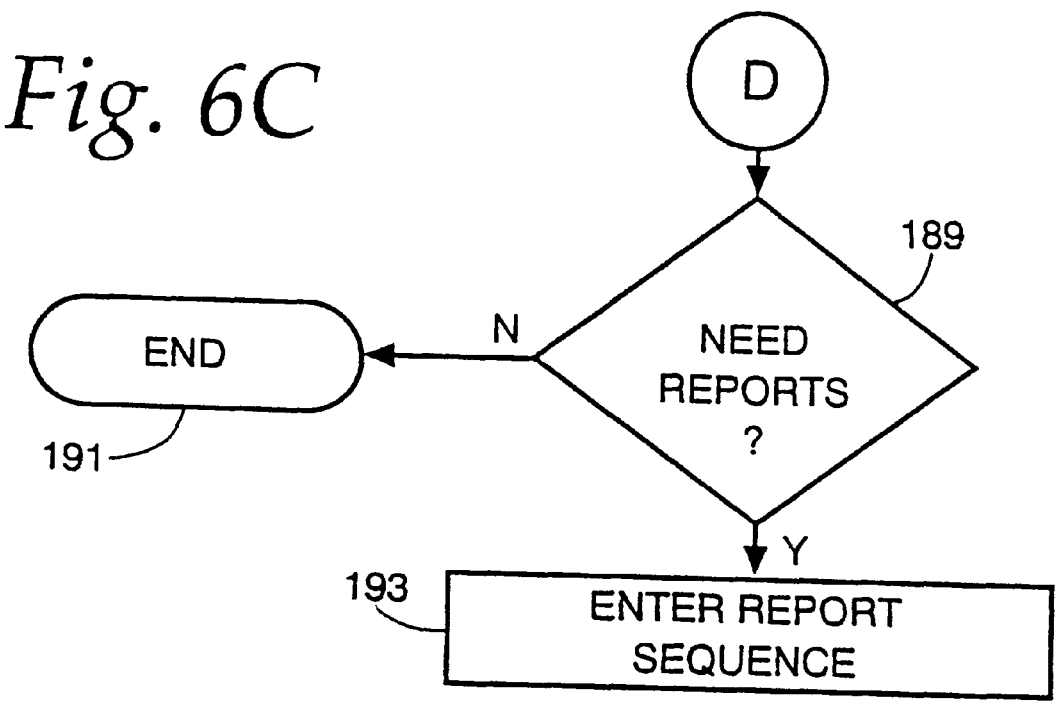

FIG. 6 is a flow diagram of the functions performed by microcomputer 90 to coordinate an assay of a plurality of prepared solutions which have been placed in wells 107 of a multi-well plate 105. Initially, the power is supplied to the apparatus of FIG. 1 and a prepared multi-well plate 105 is placed in the plate carrier system 133 (FIG. 2) of assay apparatus 98. Upon power up, microcomputer 90 performs in a block 151 a start-up routine in which communication is established with both automatic pipette 96 and assay apparatus 98 over buses 103 and 102, respectively. One important communication attribute, which is established during communication set-up, is the data rate (bank rate) for signalling between the various units. After communication set-up, microcomputer 90 proceeds to a block 153 in which the parameter values for a test are established. In the present embodiment, a test consists of the assay of one or more wells using substantially the same test parameter values. At the end of a test, a new test of the same or other wells 107 may be established using different parameter values defining a new test.

To establish test parameter values in block 153, the microcomputer 90 causes a list of parameter names to be displayed on monitor 92. Such a list is shown in FIG. 7. A human operator by interaction with keyboard 91, assigns a value to each of the displayed parameters, as is also shown in FIG. 7. The human interaction consists of the movement of a monitor cursor from one parameter name to the next, and the entry of a value for each of the parameters. After the test parameter values have been established, the flow proceeds to block 155 where the automatic pipette 96 is set-up to conduct the defined test. In block 155, the reagent quantity draw of 50 microliters, the reagent quantity pump of 50 microliters, and the syringe speed of W2 are transmitted to automatic pipette 96 via bus 103 (FIG. 1). The pipette controller 139 stores the set-up values for use in implementing draw and pump commands (FIG. 5).

A block 157 is next performed to prepare the assay apparatus 98 for the defined test. In block 157, microcomputer 90 transmits to assay apparatus 98 via bus 102, the values specified for both the excitation filter 113 and the emission filter 127. The range of possible excitation and emission filter values are shown in Tables 1 and 2, respectively. In response to the filter values, the assay controller 134 adjusts the rotatable excitation filter 113 and the rotatable emission filter 127 to the requested filter settings. The remainder of the parameter values are kept within microcomputer 90 for use in controlling the defined test.

TABLE 1

| Excitation Filters | | | Half Power |
|---|---|---|---|
| Name | Wavelength | Efficiency | Band Width |
| ex1 | 355 nm | 30% | 35 ± 4 nm |
| ex2 | 485 nm | 50% | 14 ± 2 nm |
| ex3 | 544 nm | 60% | 15 ± 2 nm |
| ex4 | 584 nm | 50% | 16 ± 2 nm |

TABLE 2

| Excitation Filters | | | Half Power |
|---|---|---|---|
| Name | Wavelength | Efficiency | Band Width |
| em1 | 460 nm | 60% | 25 ± 3 nm |
| em2 | 538 nm | 65% | 25 ± 3 nm |
| em3 | 590 nm | 30% | 14 ± 2 nm |
| em4 | 612 nm | 40% | 6 ± 1 nm |

The assay of the sample in a specified well includes the measurement of fluorescence of the sample in the specified well prior to adding reagent, the adding of reagent to the well and the measurement of fluorescence of the sample in the well after the addition of reagent. Upon completion of the assay of a well, the process repeats on other wells up to the number assigned to the number of wells parameter in block 153.

The testing of the solution in the well identified as the start well begins in block 159 in which microcomputer 90 transmits to assay apparatus 98 a plate move command specifying the X, Y coordinate address of the test well which was set equal to the start well (3,3) in a block 158. Assay controller 134 responds to the plate move command by controlling plate moving system 133 to move plate 105 to a position in which the test well (3,3) is at the sample point under the lens 121 of optical exciter/sampler 119. The excitation optical radiation from fiber 117 then excites the solution in the test well (3,3). A measure command is then transmitted in step 161 to assay apparatus 98 to measure the fluorescence of the solution in the test well. Responsive to the measure command, assay controller 134 generates a digital representation of the fluorescence magnitude sensed by photo-multiplier 131 which representation is transmitted to microcomputer 90 for storage therein in block 163. A loop comprising blocks 161, 163, 165 and 166 is performed the number of times specified in FIG. 7 for the parameter pre-reagent reads. The block 166 delays the passage through the loop so that successive measure commands are transmitted by block 161 at approximately 635 millisecond intervals.

When decision block 165 determines that the pre-reagent measurements are complete, flow proceeds to a block 167 where automatic pipette 96 is sent a fluid in command and a draw command. In response to the fluid in command, pipette controller 139 moves valve 141 to connect syringe 135 to tube 143 and in response to the draw command, 50 microliters of reagent are drawn into syringe 135. Substantially simultaneously with the transmission of the draw command, the microcomputer 90 begins the movement of the pre-reagent fluorescence values recorded in step 163 to its associated disk store 94 in block 169. The pre-reagent values are stored in a file "Test 1" as specified in the input parameters (FIG. 7), at a location allocated to pre-reagent measurements of well 3,3. Next, a block 171 is performed in which a plate move command specifying that the test well (3,3) be moved to the reagent-adding position under fluid tip 101. Following the move command of block 171 by a period of time in which the movement will be completed, a fluid-out command and a pump command are transmitted in block 173 by microcomputer 90 to automatic pipette 96. Responsive to the fluid-out and pump commands, valve 141 is switched and 50 microliters of reagent are pumped into tube 99, thus forcing 50 microliters of reagent out of fluid tip 101 into the test well. After a brief pause to allow completion of the pump operation, a step 175 is performed in which assay apparatus 98 is commanded to move the test well to the measure position under exciter/sampler 119. Advantageously, the test well is at the measure point within approximately 2 seconds of receiving the reagent.

Microcomputer 90, after a brief pause to permit the completion of plate movement, begins a loop consisting of blocks 177, 179, 181 and 182 in which 125 fluorescence measurements are taken from the test well as specified in the post-reagent input value of FIG. 7. During each trip through the loop a sample command is transmitted to assay apparatus 98 which responds thereto by returning to microcomputer 90 a digital representation of fluorescence. All returned digital representations are stored in step 179. Block 182 delays the passage through the loop so that successive measure commands are transmitted in block 17 at approximately 635 millisecond intervals. Decision block 181 counts the number of received digital fluorescent representations until the specified number of 125 such representations have been received and stored. After the 125th digital fluorescence value has been received from assay apparatus 98, the flow proceeds to block 183 where the 125 post-reagent fluorescence representations are transferred to disk store 94.

Next, a comparison block 185 is performed to determine if all of the wells specified in the test parameters have been measured. In the present example, eight wells are to be measured as indicated by the test input parameters (FIG. 7). Accordingly, flow proceeds back to block 159 after the address of the test well is set in a block 186 to the address of the next well (3,4) to be measured. In the present embodiment, the next well is the immediately adjacent well down (larger Y address) the present column of wells. When the last well of a column, e.g., 3,8 has been measured the next well is the first well of the immediately succeeding column, e.g., 4,1. After returning to block 159, tests continue for each of the remaining wells in accordance with the previously described blocks 159 through 185. After the last well has been measured, block 185 directs program flow to a block 187 in which a question is displayed on monitor 92 asking if another test is to be performed. When another test is to be performed, flow returns from block 187 to block 153 in which a subsequent test may be defined and performed as previously described. If no new test is specified by an operator, flow proceeds from decision block 187 to decision block 189. In block 189, microcomputer 90 asks via the monitor 92 whether reports are to be generated. The operator can indicate that no reports are needed at this time, and flow proceeds to a block 191 in which the assay program ends. Alternatively, when the operator indicates in block 189 that reports are to be generated flow proceeds to a block 193 where a report sequence (not shown) is entered in which data accumulated from the tests performed can be reported.

Figure 8:
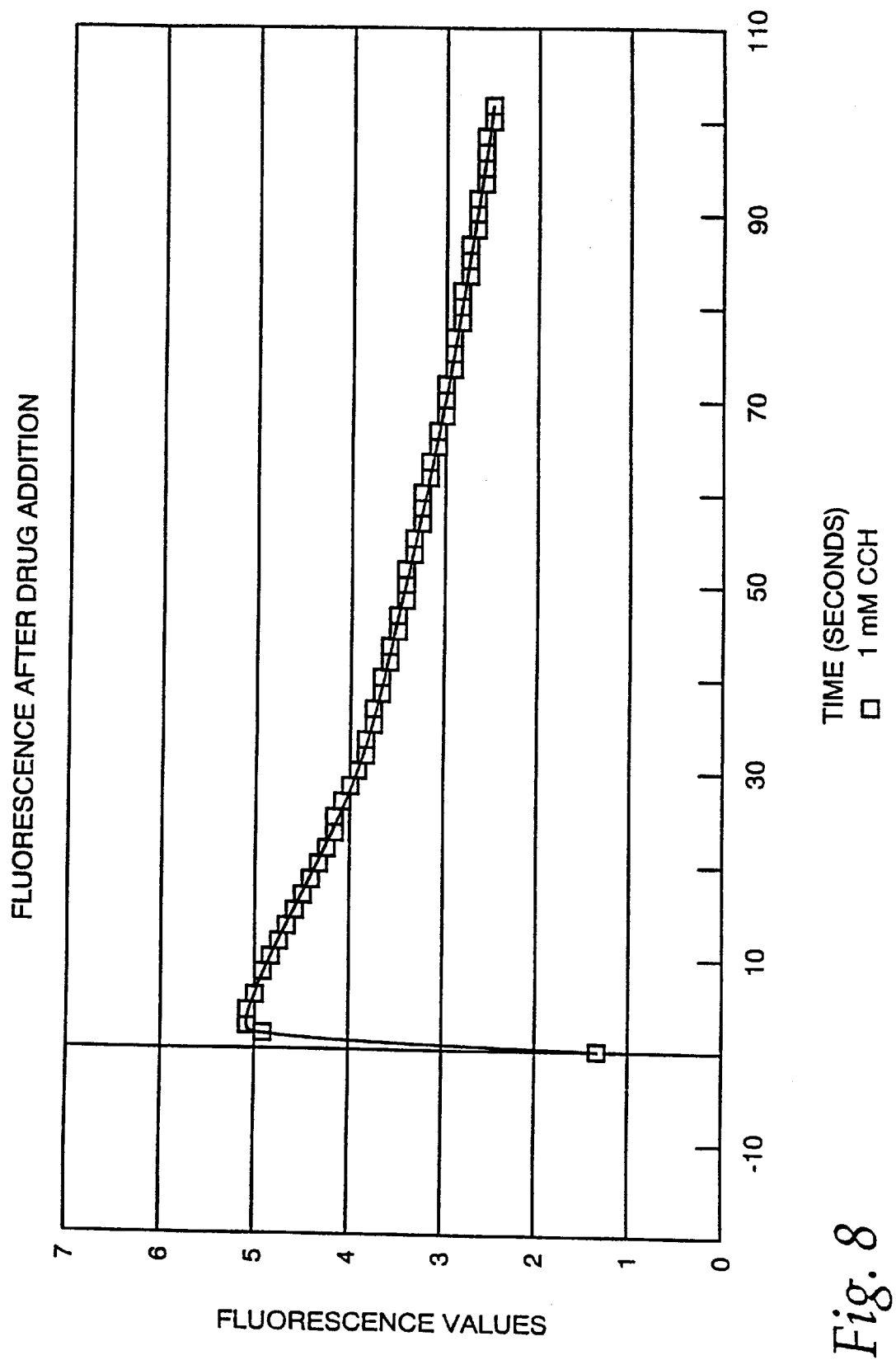
FIG. 8 shows a report of fluorescence values measured by the automated apparatus of FIG. 1.

FIG. 8 represents one report which can be generated by the apparatus of FIG. 1. The report of FIG. 8 is generated by reading the fluorescence of each well and plotting fluorescence as a function of time. The relative time of each measurement is easily determined since successive measurements for a well are taken at the previously discussed 635 millisecond intervals.

As previously described, assay apparatus 98 comprises a modified and improved Fluoroskan II. One additional modification which improves the consistency of test results entails painting the underside of the multi-well plate 105 black, so as to provide a surface having consistent non-reflective properties between the multi-well plate and the plate carrier system 133.

Figure 9:
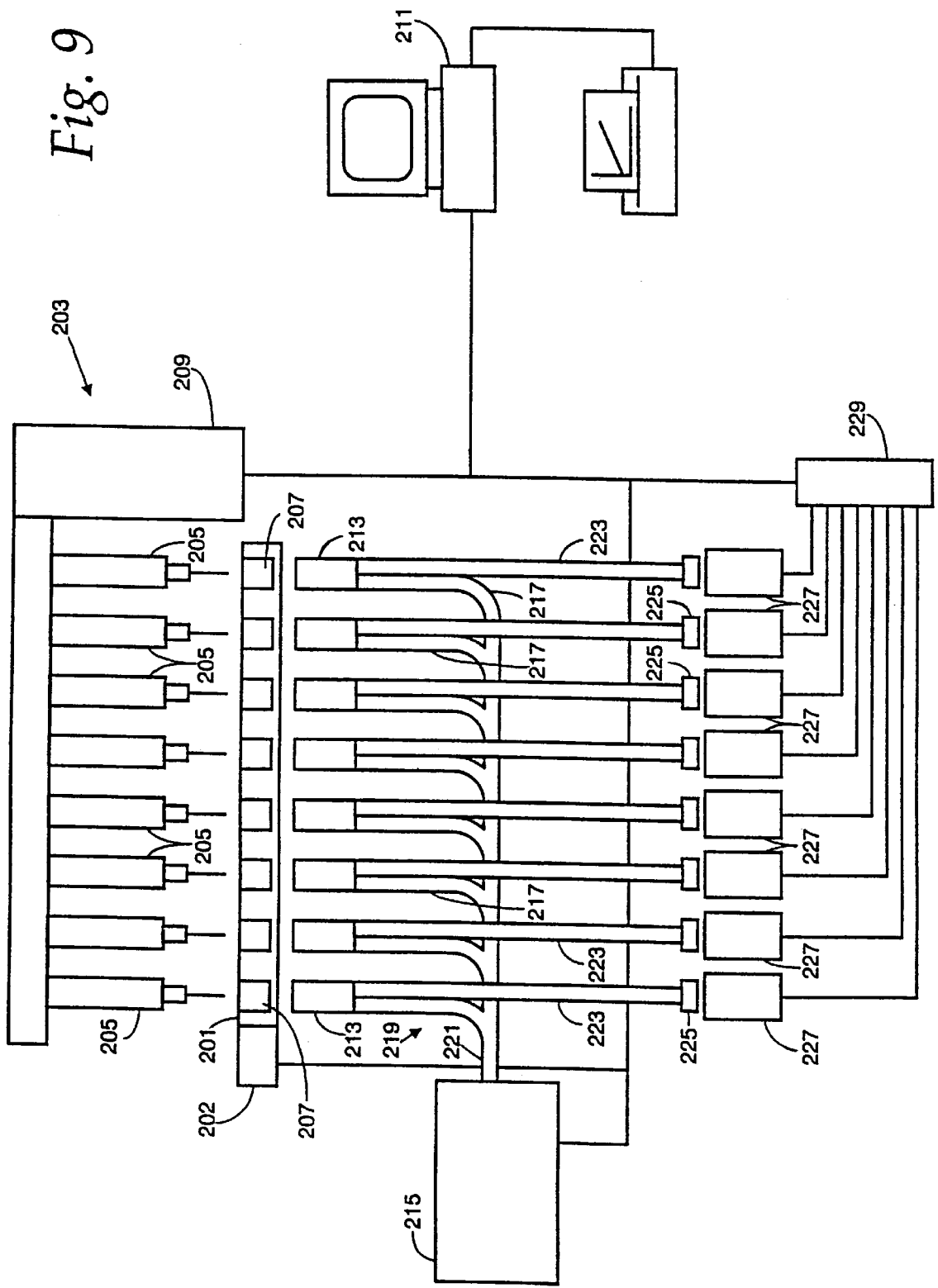
FIG. 9 is a block diagram of an embodiment of the invention which increases the efficiency of assaying.

FIG. 9 is a block diagram showing apparatus embodying the invention which speeds up the assay process by substantially simultaneously assaying samples in a plurality of sample wells 207. The principles of operation are similar to those previously described including the use of a multi-well plate 201 having 8 rows of 12 wells each as shown in FIG. 2. FIG. 9 is oriented so that the multi-well plate 201 moves into and out of the page substantially normal to the illustrated profile of the plate. Only a single column of wells 207 of plate 201 is shown. The apparatus of FIG. 9 assays an entire column of wells by substantially simultaneously exposing the samples in a column of individual wells 207 to light wave radiation and measuring the resulting emissions from beneath the plate 201 rather than from above the plate as described with regard to the embodiment of FIGS. 1–8.

The apparatus of FIG. 9 includes an automatic injection system at 203 such as the Microlab ATPlus, Biomec 1000, or Zymate II manufactured by Hamilton Co., Beckman and Zymark, respectively, which comprises eight fluid injectors 205 disposed in a linear array. The spacing between the injectors is substantially equal to the spacing between the individual wells 207. Automatic injection system 203 includes a controller 209 which responds to commands from a computer 211 by injecting equal quantities of a specified fluid into individual wells 207 by means of injectors 205.

As in the embodiment of FIGS. 1–8, a sample placed in a well 207 is assayed by exposing it to excitation light wave radiation at particular wavelengths and reading the intensity of optical emissions from the sample at other wavelengths. The apparatus of FIG. 9 applies the excitation light wave radiation and reads emissions through the plate 201. Best assay results are achieved by the use of a plate 201 which is substantially transparent to light wave radiation of the wavelengths of interest. Favorable results may be achieved by using a plate 201 made from a polystyrene material such as plates manufactured by Nunc (catalog #1-67008) or Costar (catalog #3596).

Eight optical exciter/samplers 213 are used in the present apparatus, each of which is disposed in substantial alignment with a position occupiable by a well 207. Each exciter/sampler 213 is connected to a computer controlled light source 215 by one branch 217 of a fiber optic manifold 219. As in the embodiment of FIGS. 1–8, light source 215 includes a computer controlled excitation filter for selecting the excitation light wavelengths. By design, fiber optic manifold 219 delivers to each branch 217 approximately one-eighth of the light energy transmitted from the source 215 in a main optical path 221. The main optical path 221 and branch paths 217 may comprise bundles of optical fibers each carrying light wave radiation from light source 215. Alternatively, a system of lenses can be used to focus light from light source 215 onto the individual wells.

Each exciter/sampler focuses the applied light wave energy onto the sample in one well 207 and collects and couples the light emitted from that same well to an optical emission path 223. The light conveyed by each optical emission path 223 is coupled by an emission filter 225 to a separate one of eight light detectors 227. Each light detector 227 comprises a photomultiplier tube for measuring the intensity of emitted light and for applying an analog signal representing the measured intensity to data multiplexor 229 which converts the analog signals to digital signals. Computer 211 periodically reads the outputs of the eight light detectors 227 via the data multiplexer 229 and separately records the digital data for each detector to thereby produce a plurality of digital light intensity entries for each assayed well 207. The data read arrangement could alternatively comprise detectors 227 which provide digital outputs a multiplexer 229 which responds to computer 211 by gating appropriate digital outputs to the computer.

The position of plate 201 is controlled by a plate movement apparatus 202 which operates in response to commands from computer 211. In the embodiment of FIG. 9, the row of exciter/samplers 213 is disposed directly beneath the row of injectors 205. When the samples in a column of wells 207 are to be measured, computer 211 sends commands to plate movement apparatus 202, which moves the plate 201 to place the column of wells specified in the command directly between injectors 205 and exciter/samplers 213. The position of wells 207 directly between injectors 205 and exciter/sampler 213 is referred to herein as the measure or assay position.

Figure 10A:
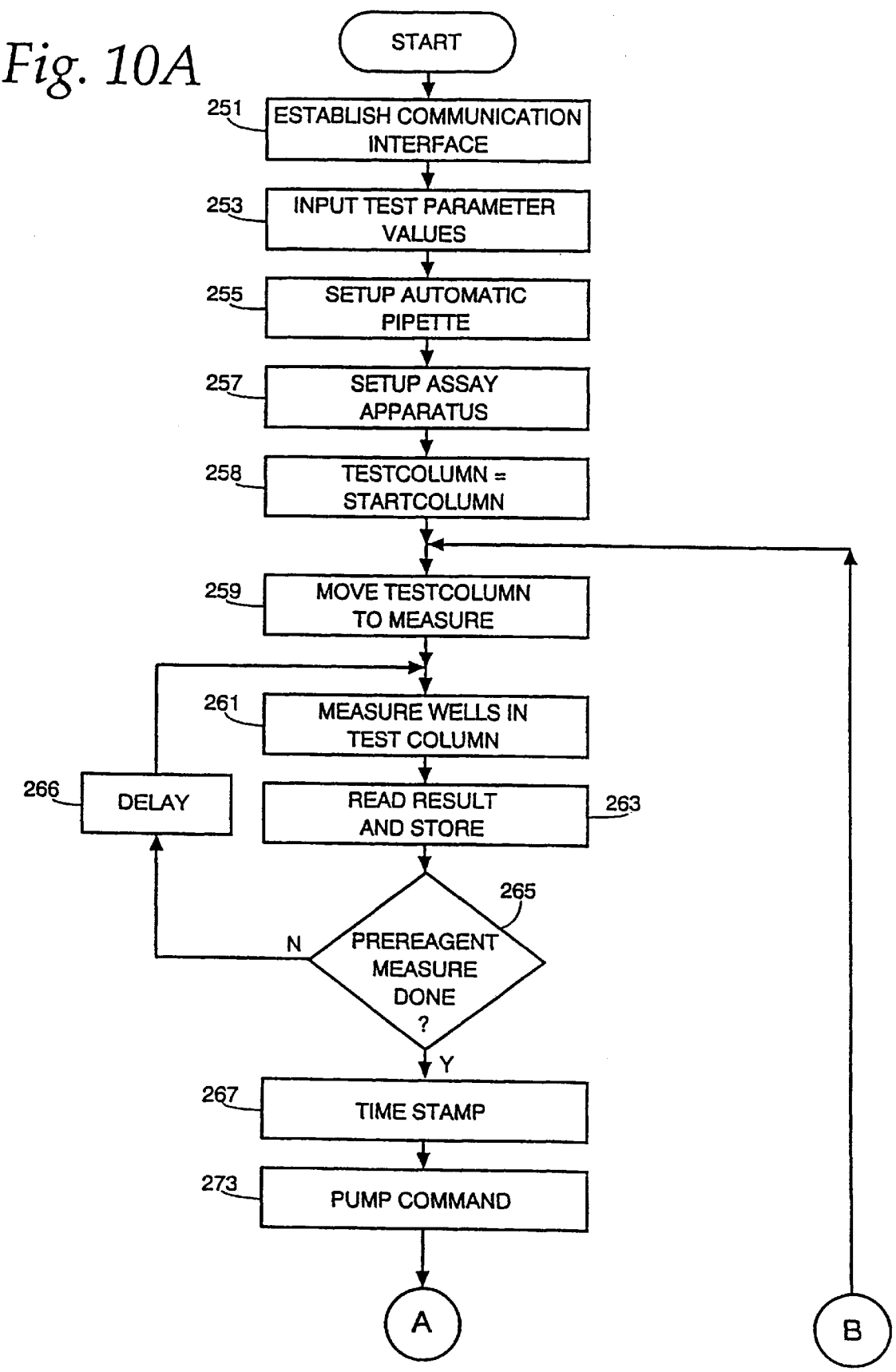
FIG. 10 is a flow diagram for the operation of the apparatus of FIG. 9.
Figure 10B:
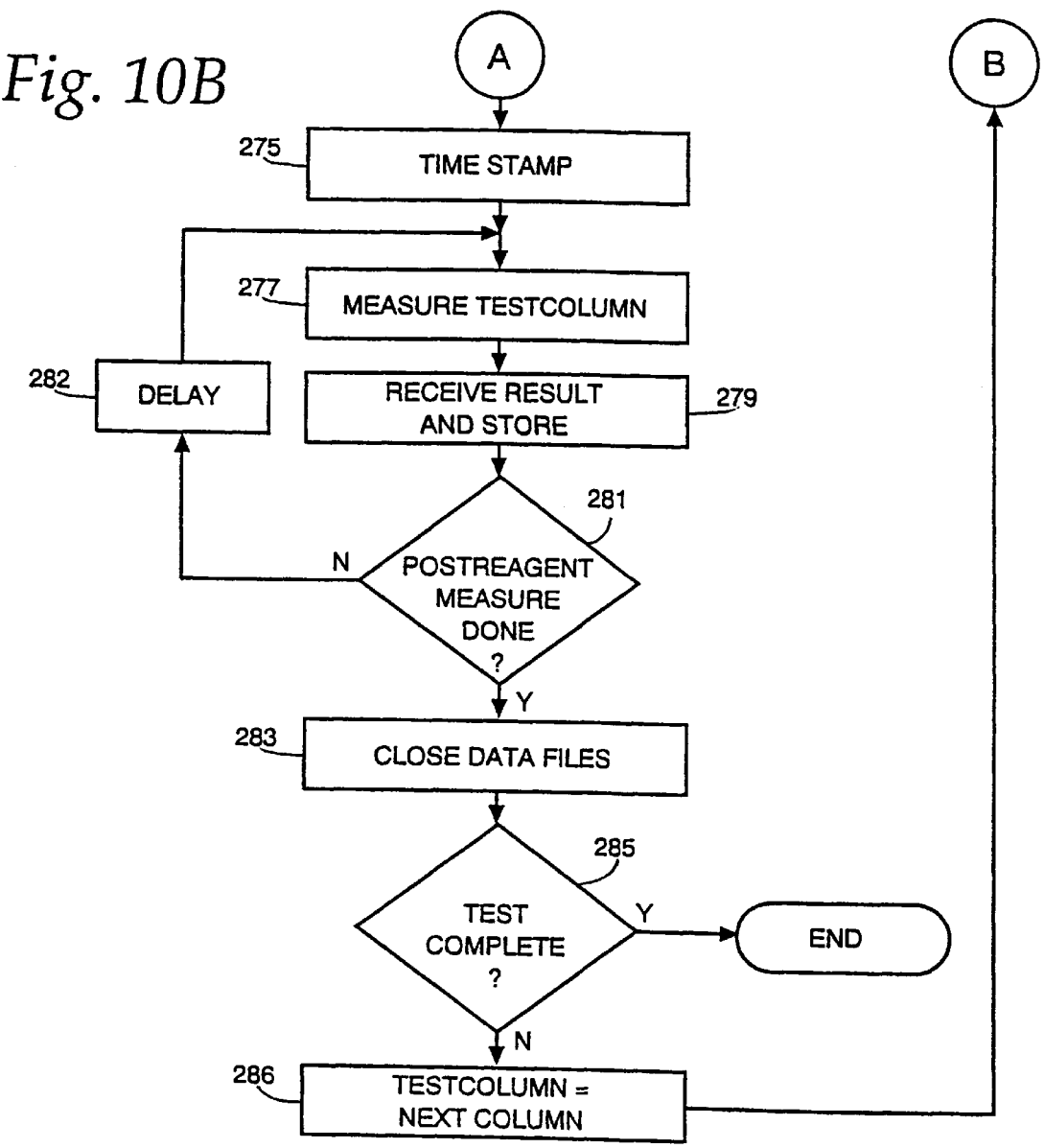

FIG. 10 is a flow diagram of the functions performed to coordinate an assay of a plurality of prepared solutions which have been placed in wells 207 of plate 201. The tests actually performed by the apparatus of FIG. 9 are similar in nature to those performed by the apparatus of FIGS. 1–8 with the additional attribute that a column of eight wells is substantially simultaneously assayed with the FIG. 9 apparatus. A test begins when a plate 201 is provided having samples to be assayed in the wells of one or more columns. Initially, the communications interfaces and other initialization occurs in a block 251 (FIG. 10) and a monitor of computer 211 is used to establish input test parameter values in a block 253.

Figures 11, 12:
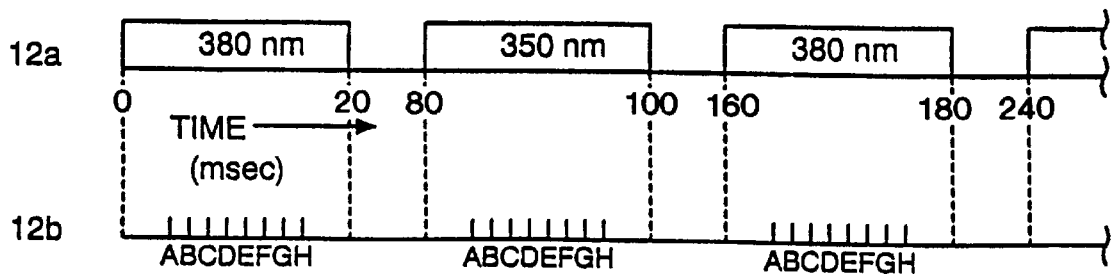
FIG. 11 represents a monitor screen displayed list of test parameters and values assigned thereto.
FIG. 12 is a graphical representation of alternating excitation light wavelengths and emission sampling.

FIG. 11 is representative of the parameter values established. As shown in FIG. 11, the test will begin with column one and proceed for 12 columns of sampled wells. After the input test parameter values are established, the automatic injection system and assay apparatus are set up in steps 255 and 257, respectively. When all of the apparatus has been initialized, a variable TESTCOLUMN is set equal to the parameter STARTCOLUMN in a step 258 and plate movement apparatus 202 is enabled in a step 259 to move column one, the STARTCOLUMN, to a position directly beneath the row of fluid injectors 205 and directly above the row of exciter/samplers 213 (the measure position). After the measure position is achieved, step 261 begins in which the excitation light wave radiation is applied to all wells in the measure position and emissions from each of the eight wells in the measure position is sampled, digitized and read by computer 211 in steps 261 and 263. A step 265 is entered by computer 211 to determine if sufficient pre-reagent measurement has occurred. If not, the process proceeds through a delay step 266 to measure, read and store another measured value. The delay step 266 is of sufficient length that well emissions are measured at approximately 100 millisecond intervals. When sufficient pre-reagent measurement has been completed as established from the test parameter values, the process proceeds from block 265 to a block 267 in which a time stamp is stored in the data file created for each of the 8 assayed wells. Such time stamp identifies the end of pre-reagent measurement. A command is then transmitted in block 273 which controls all eight fluid injectors 205 to inject the pre-established amount of reagent into their respective wells.

Upon completion of reagent addition in step 273, a reagent time stamp is stored in the data record for each of the assayed wells in a block 275. This second time stamp identifies the beginning of post-reagent measurements. After the second time stamp is stored, a new measurement loop is entered comprising blocks 277, 279, 281 and 282 in which all eight wells continue to be measured at approximately 100 millisecond rate until the pre-established number of post reagent reads has been achieved as is recognized in block 281. The per-well data files are then closed in a block 283 and a block 285 is performed to identify if the test as defined in the input parameters (FIG. 11) has been completed. In our present example, 12 columns from start column 1 through start column 12 are to be tested. Accordingly, the test will be determined not completed in block 285 and the test will proceed via block 286 to move the plate to the next column of wells (column 2) and the per-column testing is again performed. After completion of measurement for the specified 12 columns of wells, block 285 will indentify completion of the specified test and the flow proceeds to a block 287 representing the end of the data accumulation for an assay.

In the preceding example, optical emissions were measured in two distinct time periods—one before reagent was added and the other after reagent was added. The per-row assay and measurement could be done in one continuous loop from pre-reagent measurement through measurement during reagent addition and concluding after a predetermined number of post-reagent measurements. In such a situation, the previously noted time stamps (blocks 267 and 275) would identify the portion of each measurement represented in the data file whether before, during or after adding reagent. Also, it may be desirable to record a time of entry number with each intensity representing datum entered into memory.

At the completion of a test, one data file will have been stored in memory for each well assayed. The data in the data file will represent emissions from the associated well at the rate of one data entry per 100 milliseconds. Additionally, the data file will have stored therein time stamps indicating the end of pre-reagent measurements as identified in block 267 and the beginning of post-reagent measurement as marked in block 275.

In the preceding examples, a specified wave length of excitation light wave radiation was used to perform an assay. Alternatively, excitation light wave radiation of two alternating wave lengths can be employed with advantageous results. A length of time of about 100 to 200 milliseconds is generally sufficient for measuring well emissions encompassing two alternating wavelengths. The process of using two wave lengths is referred to herein as ratioing and is represented graphically in FIG. 12. For reasons which will become apparent below, the sampling interval is increased from 100 milliseconds to a period greater than or equal to 160 milliseconds when ratioing is performed. In the present embodiment, a light source produces in a recurring sequence excitation light wave radiation of 380 nanometers for 20 milliseconds, no radiation for 60 milliseconds, light wave radiation of 350 nanometers for 20 milliseconds, and no radiation for 60 milliseconds. This recurring sequence of radiation wavelengths is illustrated in line 12a of FIG. 12. Computer 211 synchronizes its light intensity measurement reading function with the pattern of radiation shown on line 12a so that the emission from each well 207 in the measure position is read once during each excitation with 380 nanometers radiation and once during each excitation with 350 nanometer wave length radiation. Each read by computer 211 of the output of a detector 227 is represented on line 12b by, a vertical line labeled A–H, eight of which occur during each 20 millisecond excitation interval. The letters A–H on line 12b each correspond to similarly labeled detector 227 of FIG. 9. Alternatively, all eight of the detectors 227 could be read substantially simultaneously.

When ratioing is being performed, the computer receives measured light intensity data stimulated alternately by the 350 and 380 nanometer radiation sources. For each 100 millisecond sampling interval, the computer 211 computes and stores the ratio of the data representing light intensity stimulated by the 350 nanometer source and the 380 nanometer source.

Figure 13:
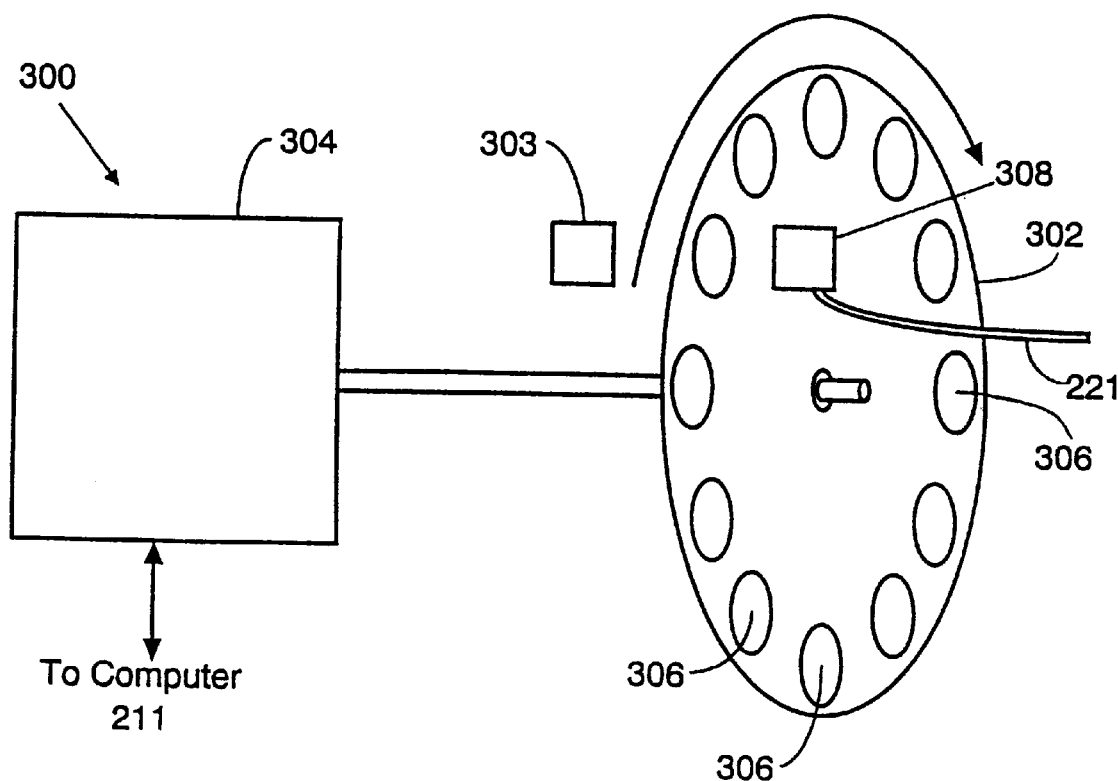
FIG. 13 shows filter wheel apparatus for producing the alternating excitation of FIG. 12.

FIG. 13 shows a filter wheel 300 which is used to provide the alternating pattern of excitation light wave radiation wave lengths shown in FIG. 12. Filter 300 includes a disc 302 having a plurality of 350 nanometer and 380 nanometer optical filter elements 306 alternately arranged with equal spacing around the center point of disc 302. An optical source 303 applies light wave radiation to one side of disc 302. As the disc is rotated by a motor 304, the light wave source 303 alternately illuminates a light accumulator 308 with 350 and 380 nanometer light. The light accumulator 308 provides excitation light wave radiation to the sample wells as shown in FIG. 13. Excitation light waves are carried from filter wheel 300 by an optical fiber path 221. The computer 211 properly synchronizes the rotation of disc 302 to achieve the excitation radiation pattern on optical path 221 shown in FIG. 12. The alternating pattern of excitation radiation wavelengths could also be generated using a system of dichroic mirrors and electronic shutters as is known in the art and described, for example, in *The Journal of Neuroscience,* November 1992, 12(11); 4202–4223.

Automatic injection system 203 of FIG. 9 is capable of delivering eight substantially equal quantities of fluid as disclosed. Automatic injection system 203 is also capable of movement from the measure position in which it is shown in FIG. 9. Such movement capability is used to advantage to provide reagent to wells 207, which may vary from column to column. For example after adding reagent to a column of wells 207 in the measure position, automatic injection system 203 may be translated, under the control of computer 211, to another position in which new and possibly different reagent is drawn into the injectors in preparation for adding reagent to a subsequent column of wells 207. After receiving the new reagent, automatic injection system 203 is moved back to the measure position in preparation for adding reagent to the subsequent column of wells.

Figure 14:
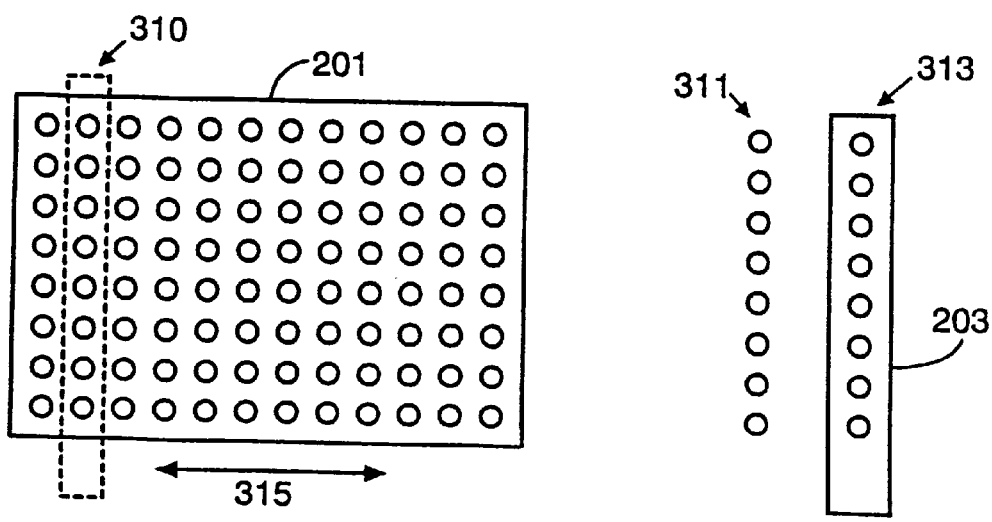
FIG. 14 is a stylized top view of the apparatus showing movement of an automatic injection system.

FIG. 14, which is a stylized top view of the apparatus, shows the advantages of injector translation. FIG. 14 includes multi-well plate 201 having a measure position 310 denoted by a dotted rectangle over the second column of wells 207. Two columns 311 and 313 of eight reagent containers are also shown in FIG. 14. After injecting reagent at the measure position, the automatic injection system 203 is moved as represented by line 315 to a position over reagent container column 313. The injectors 205 can then be filled from the reagent containers in column 313 and the automatic injection system 203 can translate back along line 315 to the measure position in preparation for adding the new reagents to column two of wells. By providing multiple columns of reagent, e.g., 311, 313, different reagents and different combinations of reagents can be added to the various columns of wells 207.

The translation and fluid drawing capabilities of automatic injection system 203 can also be used to wash the samples contained in the wells 207 before and after reagent addition, thereby saving valuable human operator time. In order to provide wash capability, a column of reagent containers, e.g., 311, is replaced with a column of appropriate cleansing buffer agents. The automatic injection system 203 is then controlled by computer 211 to draw the fluid from a column of wells to be washed, move to the column of buffer agents to draw buffer agent therefrom, return to the column 22 of wells being washed, and inject the buffer agent into them. Such automated washing of samples in wells 207 can substantially reduce the human operator time required for test performance. While the apparatus of the present invention has been described with reference to a movable plate-carrying component for moving, in a controlled stepwise sequence, a predetermined well into alignment with a stationary reagent-delivering outlet and a stationary fluorescence measurement device, it will be understood that the apparatus could be configured so that the plate carrier remains stationary and the reagent-delivering outlet and the fluorescence-measurement device move, together or independent of one another, into alignment with a predetermined well.

In accordance with another of its aspects the present invention entails an automated method for detecting activity of ion channels and/or receptors of a cell, wherein the ion channel or receptor, when activated, directly or indirectly contributes to a detectable change in the cytoplasmic level of a predetermined ion in the cell, the cytoplasm of which cell contains an indicator which is sensitive to said ion, and wherein the method is carried out in an apparatus which is capable of (1) delivering a reagent solution to a predetermined cell-containing compartment of a vessel and (2) measuring the detectable change in the cytoplasmic level of the ion in the cells of said predetermined compartment, the method comprising the steps of:

(a) providing a divided culture vessel having an array of individual compartments at least one of which contains viable cells being tested for the presence of functional ion channels and/or receptors which, when activated, are capable of directly or indirectly causing a detectable change in the concentration of the predetermined ion in the cytoplasm, the cytoplasm of said cells comprising an amount of an ion-sensitive fluorescent indicator sufficient to detect a change, if any, in the concentration of said predetermined ion;

(b) aligning a predetermined cell-containing compartment with a fluid outlet of an automatic pipette and delivering an aliquot of a solution comprising an amount of a known ion channel- or receptor-activating compound which is effective to activate said ion channel or receptor; and (c) aligning said cell-containing compartment with a fluorescence detection means and detecting and measuring for a predetermined amount of time fluorescence emitted by the ion-sensitive indicator in response to an excitation wavelength.

In accordance with another of its aspects the present invention entails an automated drug screening assay for identifying compositions having the ability to activate, potentiate, or inhibit ion channels and/or receptors of a cell, wherein the ion channel or receptor, when activated, directly or indirectly contributes to a detectable change in the cytoplasmic level of a predetermined ion in the cell, the cytoplasm of which cell contains an indicator which is sensitive to said ion, and wherein the method is carried out in an apparatus which is capable of delivering a reagent solution to a plurality of predetermined cell-containing compartments of a vessel and measuring the detectable change in the cytoplasmic level of the ion in the cells of said predetermined compartments, the method comprising the steps of:

(a) providing a divided culture vessel having one or more compartments which contain viable cells comprising functional ion channels and/or receptors which, when activated, are capable of directly or indirectly causing a detectable change in the concentration of the predetermined ion in the cytoplasm, the cytoplasm of said cells comprising an amount of an ion-sensitive fluorescent indicator sufficient to detect a change, if any, in the concentration of said predetermined ion;

(b) aligning one or more predetermined cell-containing compartments with a predetermined position;

(c) delivering to said predetermined compartment(s), with an automatic pipette, while said predetermined compartment(s) are aligned with said predetermined position, an aliquot of a solution comprising (i) an amount of a putative ion channel- or receptor-activating compound being tested for its ability to activate said ion channel or receptor or (ii) an amount of a known ion channel- or receptor-activating compound which is effective to activate said ion channel or receptor; and (d) measuring for a predetermined amount of time, while said predetermined compartment(s) are aligned with said predetermined position, fluorescence emitted by the ion-sensitive indicator in response to an excitation wavelength.

In accordance with the various assays of the present invention, cells are employed which have ion channels and/or receptors, the activation of which results in a change in the level of a cation or anion in the cytoplasm. The cytoplasm of the cells employed are loaded with a fluorescent indicator which is sufficiently sensitive to said ion. By the phrase "sufficiently sensitive fluorescent indicator" is meant a fluorescent compound which, in the presence of, and over a range of physiological concentrations of, a particular ion, is capable of producing distinguishable levels of fluorescence intensity. Preferably, a fluorescent indicator should be able to produce detectably different intensities of fluorescence in response to relatively small changes in ion concentration. The relative intensities of fluorescence when the receptors or ion channels have not been activated, as compared to when the receptors or ion channels have been activated, should differ by at least about 50% or more, preferably at least 100–200%.

One embodiment of the assays of the present invention for determining ion channel or receptor activity and compounds that affect such activity, concerns the use of "direct" assays. As used herein direct assays describe assays employing cells loaded with a fluorescent indicator which is capable of binding a specific ion, which cells have ion channels or receptors that are permeable, when activated, to said ions. Such direct assays may be performed to assay, for example, cells loaded with a calcium-sensitive fluorescent indicator and having receptors and/or ion channels that are permeable to calcium (e.g., calcium channels or N-methyl-D-aspartate (NMDA) receptors), cells loaded with a chloride-sensitive fluorescent indicator and having receptors which are permeable to chloride ions (e.g., GABA receptors), cells loaded with a sodium- or potassium-sensitive fluorescent indicator and having receptors which are permeable to sodium and/or potassium ions (e.g., kainate/AMPA receptors, nicotinic acetylcholine receptors, sodium channels or potassium channels), and so forth.

In especially preferred embodiments of the present invention cells are used which have voltage-dependent calcium channels and are loaded with a calcium-sensitive fluorescent indicator. Calcium ions may enter the cytoplasm from the extracellular medium (where the concentration of calcium ions is much greater) when voltage-dependent calcium channels are activated by depolarization of the cell membrane. Various embodiments of the assays of the present invention use cells which express functional calcium channels. In assays directed to determining the activity of calcium channels, the calcium channels are activated by depolarization of the membrane resulting from the addition of KCl to the extracellular medium.

Moreover, it is also known that certain ligand-gated ion channels, such as the GluR1 or GluR3 subtypes of excitatory amino acid (EAA) receptors and nicotinic acetylcholine receptors, are permeable to calcium ions. Assays for determining activity of such receptors, employing cells devoid of functional calcium channels (or using calcium channel-specific blockers), can be used such that receptor activity may be measured by increased levels of calcium in the cytoplasm.

In accordance with other embodiments of the assays of the invention, the activity of receptors which are ligand-gated ion channels is determined in a type of "indirect" assay which utilizes a characteristic depolarization caused by the passage of ions through ligand-gated ion channels. Such indirect assays employ cells having voltage-dependent calcium channels and the ligand-gated ion channels of interest. Activation of the ligand-gated ion channel allows ions (not calcium ions) to flow through the channel, depolarizing the cell membrane which in turn activates voltage-dependent calcium channels and results in the flow of calcium ions into the cytoplasm. The cytoplasm of the cells is loaded with a calcium-sensitive indicator. For example, activation of the nicotinic acetylcholine receptors by nicotine results in an influx of sodium ions, depolarizing the cell membrane and, consequently, activating voltage-dependent calcium channels. The degree of activation of the nicotinic receptors is measured indirectly by the flow of calcium ions through activated calcium channels. Among the known ligand-gated ion channels that could be assayed in this manner are certain kainate/AMPA-type excitatory amino acid (EAA) receptors.

Still further embodiments of the assays of the present invention concern determining the activity of receptors the activation of which initiates subsequent intracellular events in which intracellular stores of calcium ions are released for use as a second messenger. Activation of some G-protein-coupled receptors stimulates the formation of inositol triphosphate ($IP_3$, a G-protein-coupled receptor second messenger) through phospholipase C-mediated hydrolysis of phosphatidylinositol, Berridge and Irvine (1984). Nature 312: 315–21. $IP_3$ in turn stimulates the release of intracellular calcium ion stores. Thus, in accordance with certain assays of the present invention, a change in cytoplasmic calcium ion levels caused by release of calcium ions from intracellular stores is used to reliably determine G-protein-coupled receptor function. This is another type of indirect assay. Among G-protein-coupled receptors are muscarinic acetylcholine receptors (mAChR), adrenergic receptors, serotonin receptors, dopamine receptors, angiotensin receptors, adenosine receptors, bradykinin receptors, metabotropic excitatory amino acid receptors and the like. Cells expressing such G-protein-coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Another type of indirect assay involves determining the activity of receptors which, when activated, result in a change in the level of intracellular cyclic nucleotides, e.g., cAMP, cGMP. For example, activation of some dopamine, serotonin, metabotropic glutamate receptors and muscarinic acetylcholine receptors results in a decrease in the cAMP or cGMP levels of the cytoplasm. Furthermore, there are cyclic nucleotide-gated ion channels, e.g., rod photoreceptor cell channels and olfactory neuron channels [see, Altenhofen, W. et al. (1991) Proc. Natl. Acad. Sci U.S.A. 88:9868–9872 and Dhallan et al. (1990) Nature 347:184–187] that are permeable to cations upon activation by binding of cAMP or cGMP. Thus, in accordance with certain assays of the present invention, a change in cytoplasmic ion levels caused by a change in the amount of cyclic nucleotide activation of photo-receptor or olfactory neuron channels is used to determine function of receptors that cause a change in cAMP or cGMP levels when activated. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cell for this type of assay can be made by co-transfection of a host cell with DNA encoding a cyclic nucleotide-gated ion channel and a DNA encoding a receptor (e.g., certain metabotropic glutamate receptors, muscarinic acetylcholine receptors, dopamine receptors, serotonin receptors and the like, which, when activated, causes a change in cyclic nucleotide levels in the cytoplasm.

Any cell expressing a receptor protein which is capable, upon activation, of directly increasing the intracellular concentration of calcium, such as by opening gated calcium channels, or indirectly affecting the concentration of intracellular calcium as by causing initiation of a reaction which utilizes $Ca^{2+}$ as a second messenger (e.g., G-protein-coupled receptors), may be used in the assay. Cells endogenously expressing such receptors or ion channels and cells which may be transfected with a suitable vector encoding one or more such cell surface proteins are known to those of skill in the art or may be identified by those of skill in the art. Although essentially any cell which expresses endogenous ion channel and/or receptor activity may be used, it is preferred to use cells transformed or transfected with heterologous DNAs encoding such ion channels and/or receptors so as to express predominantly a single type of ion channel or receptor. Many cells that may be genetically engineered to express a heterologous cell surface protein are known. Such cells include, but are not limited to, baby hamster kidney (BHK) cells (ATCC No. CCL10), mouse L cells (ATCC No. CCLI.3), DG44 cells (see, Chasin (1986) *Cell. Molec. Genet.* 12:5551 human embryonic kidney (HEK) cells (ATCC No. CRL1573), Chinese hamster ovary (CHO) cells (ATCC Nos. CRL9618, CCL61, CRL9096), PC12 cells (ATCC No. CRL1721) and COS-7 cells (ATCC No. CRL1651). Preferred cells for heterologous cell surface protein expression are those that can be readily and efficiently transfected. Preferred cells include HEK 293 cells, such as those described in U.S. Pat. No. 5,024,939 and by Stillman et al. (1985) *Mol. Cell. Biol.* 5:2051–2060.

Exemplary cell surface proteins include, but are not limited to, cell surface receptors and ion channels. Receptors include, but are not limited to, muscarinic receptors, e.g., human M2 (GenBank accession #M16404); rat M3 (GenBank accession #M16407); human M4 (GenBank accession #M16405); human M5 (Bonner, et al., (1988) *Neuron* 1, pp. 403–410); and the like; neuronal nicotinic acetylcholine receptors, e.g., the human $\alpha_2$, $\alpha_3$ and $\beta_2$ subtypes disclosed in U.S. Ser. No. 504,455 (filed Apr. 3, 1990, which is hereby expressly incorporated by reference herein in its entirety); the human $\alpha_5$ subtype (Chini et al. (1992) *Proc. Nal. Acad. Sci. U.S.A.* 89:1572–1576), the rat $\alpha$2 subunit (Wada, et al. (1988) *Science* 240, pp. 330–334); the rat $\alpha$3 subunit (Boulter, et al. (1986) *Nature* 319, pp. 368–374); the rat $\alpha$4 subunit (Goldman, et al. (1987) *Cell* 48, pp. 965–973); the rat $\alpha$5 subunit (Boulter, et al. (1990) *J. Biol. Chem.* 265, pp. 4472–4482); the chicken $\alpha$7 subunit (Couturier et al. (1990) *Neuron* 5:847–856); the rat $\beta$2 subunit (Deneris, et al. (1988) *Neuron* 1, pp. 45–54) the rat $\beta$3 subunit (Deneris, et al. (1989) *J. Biol. Chem.* 264, pp. 6268–6272); the rat $\beta$4 subunit (Duvoisin, et al. (1989) *Neuron* 3, pp. 487–496); combinations of the rat $\alpha$ subunits, $\beta$ subunits and $\alpha$ and $\beta$ subunits; GABA receptors, e.g., the bovine $\alpha_1$ and $\beta_1$ subunits (Schofield, et al. (1987) *Nature* 328, pp. 221–227); the bovine $\alpha_2$ and $\alpha_3$ subunits (Levitan, et al. (1988) *Nature* 335, pp. 76–79); the $\gamma$-subunit (Pritchett, et al. (1989) *Nature* 338, pp. 582–585); the $\beta_2$ and $\beta_3$ subunits (Ymer, et al. (1989) *EMBO J.* 8, pp. 1665–1670); the $\delta$ subunit (Shivers, B. D. (1989) *Neuron* 3, pp. 327–337); and the like; glutamate receptors, e.g., rat GluR1 receptor (Hollman, et al. (1989) *Nature* 342, pp. 643–648); rat GluR2 and GluR3 receptors (Boulter et al. (1990) *Science* 249:1033–1037; rat GluR4 receptor (Keinanen et al. (1990) *Science* 249:556–560 ); rat GluR5 receptor (Bettler et al. (1990) *Neuron* 5:583–595); rat GluR6 receptor (Egebjerg et al. (1991) *Nature* 351:745–748); rat GluR7 receptor (Bettler et al. (1992) *Neuron* 8:257–265); rat NMDAR1 receptor (Moriyoshi et al. (1991) *Nature* 354:31–37 and Sugihara et al. (1992) *Biochem. Biophys. Res. Comm.* 185:826–832); mouse NMDA el receptor (Meguro et al. (1992) *Nature* 357:70–74); rat NMDAR2A, NMDAR2B and NMDAR2C receptors (Monyer et al. (1992) *Science*256:1217–1221); rat metabotropic mGluR1 receptor (Houamed et al. (1991) *Science* 252:1318–1321); rat metabotropic mGluR2, mGluR3 and mGluR4 receptors (Tanabe et al. (1992) *Neuron* 8:169–179); rat metabotropic mGluR5 receptor (Abe et al. (1992) *J. Biol. Chem.* 267:13361–13368); and the like; adrenergic receptors, e.g., human $\beta$1 (Frielle, et al. (1987) *Proc. Natl. Acad. Sci.* 84, pp. 7920–7924); human $\alpha$2 (Kobilka, et al. (1987) *Science* 238, pp. 650–656); hamster $\beta$2 (Dixon, et al. (1986) *Nature* 321, pp. 75–79); and the like; dopamine receptors, e.g., human D2 (Stormann, et al. (1990) *Molec. Pharm.* 37, pp. 1–6); mammalian dopamine D2 receptor (U.S. Pat. No. 5,128,254); rat (Bunzow, et al. (1988) *Nature* 336, pp. 783–787); and the like; NGF receptors, e.g., human NGF receptors (Johnson, et al. (1986) *Cell* 47, pp. 545–554); and the like; serotonin receptors, e.g., human 5HT1a (Kobilka, et al. (1987) *Nature* 329, pp. 75–79); serotonin 5HT1C receptor (U.S. Pat. No. 4,985, 352); human $5HT_{1D}$ (U.S. Pat. No. 5,155,218); rat 5HT2 (Julius, et al. (1990) *PNAS* 87, pp.928–932); rat 5HT1c (Julius, et al. (1988) *Science* 241, pp. 558–564); and the like.

Ion channels include, but are not limited to, calcium channels comprised of the human calcium channel $\alpha_1$, $\alpha_2$, $\beta$ and/or $\gamma$-subunits disclosed in commonly owned U.S. application Ser. Nos. 07/745,206 and 07/868,354, filed Aug. 15, 1991 and Apr. 10, 1992, respectively, the contents of which are hereby incorporated by reference; (see also, WO89/09834; human neuronal $\alpha_2$ subunit); rabbit skeletal muscle $\alpha$1 subunit (Tanabe, et al. (1987) *Nature* 328, pp. 313–E318); rabbit skeletal muscle $\alpha$2 subunit (Ellis, et al. (1988) *Science* 241, pp. 1661–1664); rabbit skeletal muscle $\beta$ subunit (Ruth, et al. (1989) *Science* 245, pp. 1115–1118); rabbit skeletal muscle $\gamma$ subunit (Jay, et al. (1990) *Science* 248, pp. 490–492); and the like; potassium ion channels, e.g., rat brain (BK2) (McKinnon, D. (1989) *J. Biol Chem.* 264, pp. 9230–8236); mouse brain (BK1) (Tempel, et al. (1988) *Nature* 332, pp. 837–839); and the like; sodium ion channels, e.g., rat brain I and II (Noda, et al. (1986) *Nature* 320, pp. 188–192); rat brain III (Kayano, et al. (1988) *FEBS Lett.* 228, pp. 187–194); human II (ATCC No. 59742, 59743 and *Genomics* 5:204–208 (1989); chloride ion channels (Thiemann, et al. (1992), *Nature* 356, pp. 57–60 and Paulmichl, et al. (1992) *Nature* 356, pp. 238–241), and others.

The preparation of cells which express a receptor protein capable of increasing intracellular $Ca^{2+}$ level in response to ligand binding or membrane depolarization which cells are useful for testing compounds to assess the effects of ligand-receptor interaction is exemplified in the Examples provided herewith by reference to mammalian Ltk cells which have been transfected so as to express the Type 1 human muscarinic (HM1) receptor or HEK 293 cells which have been transfected so as to express human neuronal calcium channel subunits. SHSY5Y, HEK293 or IMR32 cells which express endogenous human muscarinic receptor, nicotinic receptor or calcium channel proteins also can be useful for testing compounds in the present assay. The assays of the present invention may also be used to detect compounds which affect functional growth factor receptors, such as nerve growth factor (NGF), heparin binding growth factors and other growth factors.

Activation of the cellular receptors and/or ion channels of interest in accordance with the present invention may result in a transient increase in the level of intracellular calcium. The initial increase in calcium may be detected as an increase in fluorescence within as soon as one to two seconds after the addition of the reagent which activates the receptors and/or ion channels and is usually short-lived. Fluorescence levels in the cytoplasm typically increase to a peak value and then typically decline as excess calcium ions are removed by normal cellular mechanisms. Typically, receptor or ion channel activation causes fluorescence levels to peak within about 5 to about 45 seconds followed by reduction in fluorescence for about 2 to 20 minutes until intracellular calcium levels approach pre-activation levels. The speed at which the fluorescence can be analyzed is very important due to the kinetics of the response reaction contributed by an increase in calcium ions in the cytoplasm followed by a subsequent decrease in the level of calcium ions as they are removed from the cytoplasm.

The cells used in the assays of the invention are loaded with a fluorescent indicator which is sufficiently sensitive so as to produce detectable changes in fluorescence intensity in response to changes in the concentration of the ions in the cytoplasm. It is particularly preferred to use a fluorescent indicator which has such sensitivity in the presence of calcium ions, although indicators sensitive to other ions such as sodium ions, potassium ions, chloride ions, and the like may be employed depending on the type of receptor or ion channel activity being studied, as will be understood by the person of ordinary skill in the art. Thus, in especially preferred embodiments of the automated assays for determining functional activity of receptors or ion channels and identifying compounds which have the capacity to modulate function of such proteins (i.e., agonists, antagonists, potentiators, etc.), changes in the level of ions in the cytoplasm are detected by changes in fluorescence of an ion-sensitive indicator. Among the ion-sensitive indicators which may be employed are those disclosed in the following Table.

| ION-SENSITIVE FLUORESCENT DYES | |
|---|---|
| Fluorescent Indicator Name | Molecular Probes, Inc. Eugene, OR 97402 Catalog # |
| Calcium-sensitive | |
| Quin-2, AM | Q-1288 |
| Fura-2, AM | F-1225 |
| Indo-1, AM | I-1226 |
| Fura-3, AM | F-1228 |
| Fluo-3, AM | F-1241 |
| Rhod-2, AM | R-1244 |
| BAPTA, AM | B-1205 |
| 5,5'-dimethyl BAPTA, AM | D-1207 |
| 4,4'-difluoro BAPTA, AM | D-1216 |
| 5,5'-difluoro BAPTA, AM | D-1209 |
| 5,5'-dibromo BAPTA, AM | D-1213 |
| Calcium Green | C-3011 |
| Calcium Orange | C-3014 |
| Calcium Crimson | C-3017 |
| Fura-5 | F-3023 |
| Fura-Red | F-3020 |

-continued

| ION-SENSITIVE FLUORESCENT DYES | |
|---|---|
| Fluorescent Indicator Name | Molecular Probes, Inc. Eugene, OR 97402 Catalog # |
| Sodium-sensitive | |
| SBFI | S-1262 |
| Potassium-sensitive | |
| PBFI | P-1265 |
| Magnesium-sensitive | |
| Mag-Fura-2, AM | M-1291 |
| Mag-Indo-1, AM | M-1294 |
| Mag-Quin-2, AM | M-1299 |
| Mag-Quin-1, AM | M-1297 |
| Chloride-sensitive | |
| SPQ | M-440 |
| SPA | S-460 |

Particularly preferred assays of the present invention employ a calcium-specific fluorescent indicator, such as fluo-3, fura-2, calcium green, or the like. The most preferred calcium-specific indicator is fluo-3. See, A. Minta, et al., *J. Biol. Chem.* 264:8171–8178 (1989); J. P. Y. Kao, et al., *J. Biol Chem.* 264:8179–8184 (1989). Other fluorescent indicators for detecting ion concentrations and other fluorescent compounds such as amino acid-fluorescent indicator conjugates can also be used to detect the activity of a cell protein or the effect of a compound on cellular function wherein the fluorescent compound has differential fluorescence intensities in the presence and absence of the cellular function of interest.

The generally hydrophilic fluorescent indicators may be loaded into the cytoplasm by incubating the cells with a solution comprising a membrane-permeable derivative of the dye; however the process may be facilitated where a more hydrophobic form of the indicator is used. Thus, fluorescent indicators are known and available as more hydrophobic acetoxymethyl esters (AME) which are able to permeate cell membranes much more readily than the unmodified dyes. When the acetoxymethyl ester form of the dye enters the cell, the ester group is removed by cytosolic esterases, thereby trapping the dye in the cytosol.

Fluorescent indicator (e.g., Fluo-3) loading may be carried out at a temperature between about 5° C. and about 37° C. for between about 0.25 hours and about 20 hours, using a concentration of indicator in the range of about 5 $\mu$M to about 100 $\mu$M. While it is well within the skill of the art to determine suitable conditions for fluorescent indicator-loading, loading at 25° C. for 2–3 hours gives good results with Fluo-3. Once the cells have been loaded, they are washed with, e.g., a buffered saline solution. Our observations with Fluo-3 indicate that, after the cells are washed, they should be used in an assay within about 20 minutes.

In accordance with especially preferred embodiments of the present invention the assay reactions are carried out in a microtiter plate having a plurality of compartments (i.e., wells) seeded with viable cells which express voltage-dependent calcium channels and/or receptors of interest. Plastic microtiter plates having 96 wells arranged in a 12-by-8 array, as well as other arrays (e.g., 6-by-4 or 4-by-3), are well known in the art. Although any number of cells capable of eliciting a detectable fluorescence signal in an assay may be used, the number of cells seeded into each well may desirably be chosen so that the cells are at or near confluence, but not overgrown, when the assays are conducted, so that the fluorescence signal-to-noise ratio is increased.

After the cells have been loaded with the fluorescent indicator, the cells in the microtiter plate are washed with buffer to remove excess indicator and suitable assay buffer is added to the respective wells. If desired, the assays may be carried out in replicate wells (duplicate, triplicate, etc.) for statistical purposes. The buffer conditions in the individual wells should be such that the ion channels or receptors of interest in the assay will remain substantially at rest (i.e., not activated) until stimulated by addition of an aliquot of reagent which activates the ion channel or receptor of interest. In some instances, the buffer may desirably contain compositions that do not activate the receptor or ion channel of interest but that facilitate activation of receptor/ion channel when the activating reagent is added to the well to initiate the assay. For instance, some voltage-dependent ion channels (e.g., the N-type calcium channel) are sensitive to the resting potential of the cell membrane and may be less susceptible to activation at more positive resting potentials. In such cases, it may be desirable to adjust the buffer conditions to include compounds that serve to lower the membrane potential (e.g., ionophores, valinomycin, etc.) thereby facilitating activation of the channel by depolarization of the membrane. The microtiter plate is placed in the apparatus of the invention just prior to starting a series of individual assays in the respective wells. The assays may be carried out at a temperature of about 10° C. to about 37° C., more preferably at about 20° C. to about 30° C.

Prior to starting the sequence of multiple assays, certain variables may be keyed into a controlling computer such as a microprocessor. As described in detail hereinbefore, variables may include the number and location (i.e., column, row) of the first well(s) to be assayed, the number of data points to be collected, the time period for obtaining and recording fluorescence readings (pre-reagent and post-activation), the filter settings for excitation and emission wavelengths, the aliquot size to be delivered by the automatic pipettor, and the like.

The apparatus of tie present invention coordinates the movement of the microtiter plate (and, preferably, the reagent-adding device), reading of the fluorescence signal, and initiation of the assay reaction by addition of an aliquot of reagent to an individual well to activate the ion channels or receptors of interest. In a specific embodiment, the first well to be tested is aligned with optical exciter/sampler 119 and pre-reagent fluorescence emission from the cells is measured for a short period of time. Then the well is aligned with the fluid tip 101 of automatic pipette 96 where an aliquot of a suitably concentrated reagent is added so as to initiate the assay reaction, and then realigned with the optical exciter/sampler.

Any compound which is known to activate ion channels or receptors of interest may be used to initiate the assay. Choosing an appropriate ion channel- or receptor-activating reagent depending on the ion channel or receptor of interest is within the skill of the art. Direct depolarization of the cell membrane to determine calcium channel activity may be accomplished by adding a potassium salt solution having a concentration of potassium ions such that the final concentration of potassium ions in the cell-containing well is in the range of about 50–150 mM (e.g., 50 mM KCl). With respect to ligand-gated receptors and ligand-gated ion channels, ligands are known which have affinity for and activate such receptors. For example, nicotinic acetylcholine receptors are known to be activated by nicotine or acetylcholine; similarly, muscarinic acetyl choline receptors may be activated by addition of muscarine or carbamylcholine. Where it is desirable to conduct assays concerning compounds having unknown or putative ligand activity, the assays may be initiated by delivering a reagent comprising the compound through fluid tip 101 of automatic pipette 96 or by adding the compound to the wells and then delivering a known activator through fluid tip 101 of automatic pipette 96.

Agonist assays may be carried out on cells known to possess ion channels and/or receptors to determine what effect, if any, a compound has on activation or potentiation of ion channels or receptors of interest. Agonist assays also may be carried out using a reagent known to possess ion channel- or receptor-activating capacity to determine whether a cell expresses the respective functional ion channel or receptor of interest.

Contacting a functional receptor or ion channel with agonist typically activates a transient reaction; and prolonged exposure to agonist may desensitize the receptor or ion channel to subsequent activation. Thus, in general, the assays for determining ion channel or receptor function should be initiated with addition of agonist (i.e., in the reagent solution used to initiate the reaction). The potency of a compound having agonist activity is determined by the detected change in fluorescence in the cells (typically an increase, although activation of certain receptors causes a decrease) as compared to the level of fluorescence in either the same cell, or substantially identical cell, which is treated substantially indentically except that reagent lacking the agonist (i.e., control) is added to the well. Where an agonist assay is performed to test whether or not a cell expresses the functional receptor or ion channel of interest, known agonist is added to test-cell-containing wells and to wells containing control cells (substantially identical cell that lacks the specific receptors or ion channels) and the levels of fluorescence are compared. Depending on the assay, cells lacking the ion channel and/or receptor of interest should exhibit substantially no increase in fluorescence in response to the known agonist. A substantially identical cell may be derived from the same cells from which recombinant cells are prepared but which have not been modified by introduction of heterologous DNA. Alternatively, it may be a cell in which the specific receptors or ion channels are removed. Any statistically or otherwise significant difference in the level of fluorescence indicates that the test compound has in some manner altered the activity of the specific receptor or ion channel or that the test cell possesses the specific functional receptor or ion channel.

In one of the preferred embodiments of the present invention which pertain to automated drug screening assays for identifying compounds which have the ability to modulate ion channels or receptors of interest, it is contemplated that each of the individual wells (or duplicate wells, etc.) contain a distinct cell type, or distinct recombinant cell line expressing a homogeneous population of a receptor or ion channel of interest, so that the compound having unidentified activity may be screened to determine whether it possesses modulatory activity with respect to one or more of a variety of functional ion channels or receptors.

In another aspect of the preferred embodiments of the invention, it is contemplated that each of the individual wells contain the same cell type so that multiple compounds (obtained from different reagent sources in the apparatus or contained within different wells) can be screened and compared for modulating activity with respect to one particular receptor or ion channel type.

In another of its aspects the invention entails automated antagonist assays. Antagonist assays, including drug screening assays, may be carried out by incubating the cells having functional ion channels and/or receptors in the presence and absence of one or more compounds, added to the solution bathing the cells in the respective wells of the microtiter plate for an amount of time sufficient (to the extent that the compound has affinity for the ion channel and/or receptor of interest) for the compound(s) to bind to the receptors and/or ion channels, then activating the ion channels or receptors by addition of known agonist, and measuring the level of fluorescence in the cells as compared to the level of fluorescence in either the same cell, or substantially identical cell, in the absence of the putative antagonist.

As will be understood by the person of ordinary skill in the art, compounds exhibiting agonist or antagonist activity in an ion channel or receptor assay will either increase or decrease intracellular ion levels (agonist) or inhibit (antagonist) an increase or decrease in the intracellular concentration of ions after activation of the ion channels or receptors of interest. It is desirable to measure the amount of agonist or antagonist activity in a linear range of the assay system, such that small but significant increases or decreases in fluorescence relative to control well (e.g., devoid of the test compound) may be observed. It is well within the skill of the art to determine a volume and concentration of a reagent solution which causes a suitable activation response in cells so that potentiation and/or inhibition of the ion channels or receptors of interest may be reliably detected.

With respect to voltage-dependent calcium channels, certain agonists are known (e.g., Bay K 8644) which act to increase the duration of time that some calcium channels remain open after membrane depolarization but do not cause depolarization. Because such agonists bind to ion channels without activating them, they may be assayed in a manner similar to that used for an antagonist assay except that the observed result will be increased fluorescence in the test wells.

Immediately after addition of the reagent which initiates activation of the ion channels or receptors of interest, the plate is moved, if necessary, so that the cell-containing assay well is positioned for measurement of fluorescence emission. Because a change in the fluorescence signal may begin within the first few seconds after addition of ligands or other reagents, it is desirable to align the assay well with the fluorescence reading device as quickly as possible, times of about two seconds or less being desirable. In preferred embodiments of the invention, where the apparatus is configured for detection through the bottom of the well(s) and reagent-addition is from above the well(s), fluorescence readings may be taken substantially continuously, since the plate does not need to be moved for addition of reagent. The well and fluorescence-reading device should remain aligned for a predetermined period of time suitable to measure and record the change in intracellular ion, e.g., calcium, concentration. In preferred embodiments of the invention the fluorescence after activation is read and recorded until the fluorescence change is maximal and then begins to reduce. An empirically determined time period may be chosen which covers the transient rise and fall (or fall and rise) of intracellular ion levels in response to addition of the reagent. It has also been found, surprisingly, that painting the bottom of the wells black reduces the background fluorescence and thereby decreases the noise level in the Fluoroskan II, where the apparatus is configured to detect fluorescence from above the plate.

After finishing reading and recording the fluorescence in one well, the just described apparatus steps are repeated with the next well(s) in the series so as to measure pre-reagent fluorescence, add reagent and measure and record the transient change, if any, in fluorescence. The apparatus of the present invention is programmable to begin the steps of an assay sequence in a predetermined first well (or row or column of wells) and proceed sequentially down the columns and across the rows of the plate in a predetermined route through well number n.

In assays of cells containing receptors and/or ion channels that, when activated, cause an increase in intracellular calcium ion concentration, the fluorescence data from replicate wells of cells treated the same with agonist are collected and recorded (e.g., stored in the memory of a computer) for calculation of fluorescence signal-to-noise ratio (S/N) and/or the intracellular calcium concentration signal-to-noise ratio. Fluorescence readings, corresponding to $F_B$, $F_D$, $F_{max}$, $F_{min}$, can be obtained from each drug-treated well. These values (as defined below) can be inserted into Equations 1 through 4 to calculate the signal-to-noise ratios of fluorescence (F) and of intracellular calcium concentration ($Ca_i$).

$$FS/N = \frac{F_D - F_{min}}{F_B - F_{min}} \qquad \text{Equation 1}$$

$$FS/N = \frac{F_D}{F_B} \qquad \text{Equation 2}$$

$$FS/N = \frac{F_D - F_0}{F_B - F_0} \qquad \text{Equation 3}$$

$$Ca_i S/N = \frac{\frac{F_D - F_{min}}{F_{max} - F_D} \times 450 \; (K_d \text{ for fluo-3})}{\frac{F_B - F_{min}}{F_{max} - F_B} \times 450} \qquad \text{Equation 4}$$

$F_B$ = fluorescence reading before drug addition $F_D$ = peak or maximal fluorescence reading after drug addition $F_{max}$ = fluorescence reading after cell lysis with Triton X-100

$F_{min}$ = fluorescence reading after quenching with EGTA $F_0$ = fluorescence reading of cells in wells plus buffer but without fluorescent indicator As shown in Equation 1, the fluorescence signal-to-noise ratios represent the ratio of the fluorescence measured in the presence of the drug (signal) and the fluorescence measured in the absence of drug (noise). The background fluorescence, $F_{min}$ (measured after EGTA quenching), can be subtracted from both the signal fluorescence and the noise fluorescence. Alternatively, meaningful results can be obtained by simply calculating fluorescence signal-to-noise as the ratio of the peak fluorescence after addition of a compound and the total fluorescence before addition of a compound (Equation 2). Fluorescence signal-to-noise ratios can further be obtained by subtracting the fluorescence measured in cells that do not contain indicator ($F_0$) from $F_D$ and $F_B$ and taking the ratio of the differences (Equation 3). The intracellular calcium signal-to-noise ratios represent the ratio of the intracellular calcium concentrations in the presence of the drug and in the absence of drug as calculated from the fluorescence measurements (see Equation 4).

In assays of antagonists of receptors or ion channels that, when activated, cause an increase in intracellular calcium ion concentration, the results are expressed as a percentage of the maximal response caused by a known agonist. The maximal fluorescence increase caused by a known agonist is defined as being 100% response. The maximal fluorescence recorded after addition of agonist to wells containing an active antagonist is detectably lower than the 100% response. Thus, the fluorescence data from such an antagonist assay are used to calculate the percentage of maximal response as follows:

$$\frac{\left(\frac{F_{(agonist+antagonist)}}{F_B}\right)-1}{\left(\frac{F_{(agonist)}}{F_B}\right)-1} \times 100 \qquad \text{Equation 5}$$

The fluorescence indicator-based assays of the present invention are thus useful for rapidly screening compounds to identify those that modulate any receptor or ion channel whose activity ultimately results in an altered concentration of ions in the cytoplasm of a cell. In particular, the assays can be used to test functional ligand-receptor or ligand-ion channel interactions for cell receptors including ligand-gated ion channels, voltage-gated ion channels, G-protein-coupled receptors and growth factor receptors.

While the preferred assays of the present invention involve detecting differences in fluorescence intensities based on changes in the level of fluorescence intensity of an ion-sensitive fluorescent indicator caused by changes in the level of a particular ion in the cytoplasm, it will be understood that the assays of the present invention encompass measuring a detectable change of a solution as a consequence of a cellular event which allows a compound, which is capable of differential fluorescence, to change its fluorescence intensity in response to the cellular event. By selecting a particular fluorescent compound which is capable of differential fluorescence intensities upon the occurrence of a cellular event, various assays which are within the scope of the present invention may be performed. For example, assays for determining the capacity of a compound to induce cell injury or cell death may be carried out by loading the cells with a pH-sensitive fluorescent indicator such as BCECF (Molecular Probes, Inc., Eugene, Oreg. 97402, Catalog #B1150) and measuring cell injury or cell death as a function of changing fluorescence over time.

Furthermore, assays may be based on an increase in fluorescence when a fluorescent indicator is released from the cytoplasm of a cell. For example, assays for determining the ability of a chemotherapeutic agent to kill malignant cells may be carried out using malignant cells which are loaded with a fluorescent indicator which is sensitive to an ion (e.g., $Ca^{2+}$) wherein the ion is present at much greater concentration in the solution bathing the cell than in the cytoplasm, such that cytotoxicity of the test compound is measured by the flow of dye out of the cell into the extracellular medium (i.e., from an environment of low calcium concentration to an environment of high calcium concentration) resulting in an increased intensity of fluorescence emission by the indicator.

Moreover, the differential intensity of fluorescence, which is detected by the assay methods of the present invention, may be caused by a modification of a compound which can exist in either a non-fluorescing or fluorescing form and wherein occurrence of the cellular event results in a modification which allows the non-fluorescing form of the compound to become fluorescent. In an example of such an assay, the function of certain neurotransmitter transporters which are present at the synaptic cleft at the junction between two neurons may be determined by the development of fluorescence in the cytoplasm of such neurons when conjugates of an amino acid and fluorescent indicator (wherein the fluorescent indicator of the conjugate is an acetoxymethyl ester derivative e.g., 5-(aminoacetamido) fluorescein; Molecular Probes, Catalog #A1363) are transported by the neuro-transmitter transporter into the cytoplasm of the cell where the ester group is cleaved by esterase activity and the conjugate becomes fluorescent.

In a further example of such an assay, the function of receptors whose activation results in a change in the cyclic nucleotide levels of the cytoplasm may be directly determined in assays of cells that express such receptors and that have been injected with a fluorescent compound that changes fluorescence upon binding cAMP. The fluorescent compound comprises cAMP-dependent-protein kinase in which the catalytic and regulatory subunits are each labelled with a different fluorescent-dye [Adams et al. (1991) Nature 349:694–697]. When cAMP binds to the regulatory subunits, the fluorescence emission spectrum changes; this change can be used as an indication of a change in cAMP concentration.

All of the patents, publications and commonly owned patent applications referred to herein are hereby expressly incorporated by reference into this application.

The following examples are included for illustrative purposes only and are not intended to limit the scope of the invention.

EXAMPLE 1

Preparation of Stably Transfected Mammalian Cell Lines That Express Human M1 Muscarinic Acetylcholine (HM1) Receptors Stable cell lines expressing recombinant HM1 receptors for use in the automated assay were prepared. Ltk⁻ cells, which are thymidine kinase-deficient mouse fibroblast cell lines, were stably co-transfected with a plasmid containing DNA that encodes HM1 and a selection plasmid containing either the wild-type or crippled thymidine kinase gene.

A. Preparation of Transfected Mammalian Cell Lines

Cell lines that can be used as host cells include the following: HEK 293, which are human embryonic kidney cells such as those described in U.S. Pat. No. 5,024,939 to Garman, and by Stillman, et al. Mol. Cell. Biol. 5:2051–2060 (1985) or available from ATCC (accession #CRL 1573); Ltk⁻ cells, which are available from ATCC (accession #CCL1.3); COS-7 cells, which are available from ATCC (accession #CRL 1651); DG44 cells (see, e.g., L. Chasin (1986) Cell. Molec. Genet. 12, p. 555), which are Chinese hamster ovary (CHO) cells; related CHO-based cells available as ATCC accession #CRL 9618, #CCL61 or CRL 9096; baby hamster kidney (BHK) cells (ATCC #CCL10).

B. DNA that Encodes M1 Receptor was Cloned and Inserted into a Mammalian Cell Expression Plasmid The sequence of the HM1-encoding DNA fragment is described in Allard, et al. (1987), Nucl. Acids Res. 15, p. 10604. It can be prepared by synthesizing the cDNA construct based on the sequence described by Allard, et al. or it can be isolated by screening a human genomic DNA library. It has been isolated by screening a human genomic library that contains 2.5–4.5 kb-sized EcoRI fragments in the γgt11 vector, with an oligonucleotide homologous to nucleotides 250–279 of the HM1 gene sequence. Screening conditions employed were as follows:

hybridization: 20% deionized formamide, 5×Denhardt's, 6×SSPE, 0.2% SDS, 200 μg/ml sonicated herring sperm DNA, 42° C.

wash: 0.2×SSPE, 0.2% SDS, 50° C.

A positive clone was identified and confirmed to encode the HM1 receptor by DNA sequencing. The EcoRI insert of that clone was isolated and inserted into the EcoRI site of pIBI24 (International Biotechnologies, Inc., New Haven, Conn.), yielding clone pIBI24/HM1.

The HM1-encoding fragment of pIBI24/HM1 was modified for insertion into the SV40 promoter-based plasmid pSV2dhfr (see Subramani, et al. (1981) Mol. Cell. Biol. 1, pp. 854–864). Fifty nanograms of the 1.97 kb BamHI fragment from pIBI24/HM1 were ligated with 50 ng of BamHI-digested M13mp18. The ligation was transformed into E. coli strain JM103, and Amp$^R$ colonies were selected. Correct plasmid was identified by the presence of a 1.45 KpnI digestion fragment. Template was prepared from this plasmid to introduce an EcoRI site immediately before the initiation codon of the human HM1 coding region. This was accomplished by standard mutagenesis using the following oligonucleotide to introduce an EcoRI site adjacent (and 5') to the translation initiation codon of the human HM1 coding region:

5'-CCCCAGCCCC ACCTTGAATT CATGAACACT TCAGCC-3'. (Seq. ID No. 1).

The mutagenesis products were transformed into JM103 and screened on plaque lifts with an oligonucleotide having the sequence:

5'-CACCTTGAAT TCATGAAC-3' (Seq. ID No. 2).

Four of the positive clones were subjected to dideoxy sequencing and all were found to have the correct sequence, i.e., an added EcoRI site immediately 5' of the 5' ATG. One of the positive sequence clones, mHM1AChR103, was selected. Oligonucleotide-directed mutagenesis employing the following oligonucleotide was used to introduce an additional EcoRI site adjacent (and 3') to the translation termination codon of the human HM1 coding sequence:

5'-CTCCCGCCAA TGCTGAGAAT TCTATCTCCT GCATCCC-3' (Seq. ID No. 3).

Mutagenesis products were transformed into JM103 and screened on plaque lifts with an oligonucleotide of the following sequence:

5'-CTGAGAATTCTATCTCC-3' (Seq. ID No. 4).

Positive clones were identified and four were sequenced to confirm that the EcoRI site had been introduced and that remainder of the sequence was unaltered. The four sequenced clones had the correct sequence.

One of the sequenced clones, M3HM1AR04, was digested with EcoRI and the 1.4 kb fragment representing the human M1 coding region was gel purified and eluted using DE-81 paper. Sixty nanograms of the 1.4 kb fragment were ligated with 20 ng of EcoRI-digested pUC19. Correct clones were identified by the presence of a 1.2 kb KpnI fragment. One of these was chosen and designated pHM1RO2. The 1.4 kb EcoRI fragment was removed from pHM1RO2 and inserted (38.5 ng) into 50 ng of EcoRI-digested pSV2dhfr. The resulting product was transformed into DH5α (Sambrook, et al., Molecular Cloning, 2nd ed., Cold Spring Harbor Lab, 1989, p. 10) cells and AmpR colonies were selected. Of the selected colonies, those that, upon digestion with EcoRI, yielded fragments of 1.4 and 5.0 kb and, upon digestion with PvuII, yielded fragments of 250, 1150, and 5000 bp, contained the insert in pSV2dhfr in the correct orientation. The final HM1 expression vector was called HM1pSV2dHFR.

C. Preparation of TK$^+$ (Thymidine Kinase) Selection Plasmids

Either pThx59 (Zipser, et al. (1981) Proc. Natl. Acad. Sci. 78, pp. 6276–6280), which encodes the wildtype TK gene, or pThx24 (ibid.), which encodes a crippled TK gene, was co-transfected into Ltk$^-$ cells along with the muscarinic receptor-expressing plasmids in order to prepare stably transfected Ltk cells that express the cloned HM1 receptor on the cell surfaces.

D. Preparation of Stably Transfected Cell Lines Expressing Functional Human M1 Muscarinic Acetylcholine Receptor Stable HM1-expressing cell lines were prepared using calcium phosphate transfection to introduce the plasmid DNA (see, Wigler, et al. (1979), Proc. Natl. Acad. Sci. 76, pp. 1373–1376). Briefly, Ltk cells were grown in nonselective medium, D+10, which contains Dulbecco's modified Eagle's medium+10% calf serum, in a 10 cm-sized dish, to 20% confluence. The two circular plasmids, the TK$^+$ plasmid and the HM1-containing plasmid, were co-precipitated with CaPO$_4$ and added to the cell monolayer. The vector concentrations were as follows:

Thx24:HM1pSV2dHFR 2 μg:2 μg/ml

Thx59:HM1pSV2dHFR 0.25 μg:2 μg/ml

The final concentration of DNA was adjusted to 20 to 40 μg/ml by adding Ltk$^-$ or pUc DNA. The transfected cells were cultured for two days in nonselective medium. After two days, the cells were passed, non-selective media was replaced with HAT medium (D+10+15 μg/ml hypoxanthine+1 μg/ml aminopterin+5 μg/ml thymidine), and the cells were cultured for 10–15 days, during which time the cells were "fed" fresh selective (HAT) medium every 3–4 days. After 10–15 days, colonies or clones appeared which indicated acceptance and expression of at least the plasmid carrying the TK gene. Colonies were transferred into separate wells of a 24-well dish and grown in selective medium for seven days. Individual clones were then transferred into 6-well dishes and grown for another seven days in selective medium. To provide cells for freezing and subsequent molecular and functional receptor analyses, the individual clones in the 6-well dishes were passed to 100-cm dishes. Two of the resulting cell lines were designated LM124-3 and LM159-10.

EXAMPLE 2

Preparation of Recombinant Mammalian Cell Lines by Transfection with cDNAs Encoding Human Neuronal Calcium Channel Subunits Complementary DNAs encoding α1, α2 and β subunits of human neuronal voltage-dependent calcium channels (VDCC) were isolated as described in co-owned U.S. patent application Ser. Nos. 745,206 and 868,354, filed Aug. 15, 1991, and Apr. 10, 1992, respectively, the disclosure of which is hereby incorporated by reference. These cDNAs were separately incorporated into mammalian expression vectors for use in recombinant expression of calcium channels in mammalian cells.

A. Calcium Channel Subunit Gene Expression Vectors

Particularly preferred vectors for transfection of mammalian cells are the pSV2dhfr expression vectors (which comprises the SV40 early promoter, mouse dhfr gene, SV40 polyadenylation and splice sites and sequences necessary for maintaining the vector in bacteria), cytomegalovirus (CMV) promoter-based vectors such as pCMV or pCDNA1, or MMTV promoter-based vectors.

To construct mammalian expression vectors for use in recombinant expression of human neuronal voltage-dependent calcium channel subunits, portions of partial subunit cDNAs were ligated with pCDNA1 (Invitrogen, San Diego, Calif.) as described in detail in U.S. Ser. Nos. 745,206 and 868,354. In constructing $\alpha_{1D}$ and $\alpha_{1B}$ subunit expression vectors, partial α1 subunit cDNAs were ligated with digested pCDNA1, and the resulting constructs, each containing a full-length al subunit-encoding DNA under the regulatory control of the CMV promoter, were called pVDCCIII(A) and pCDNAα$_{1B\text{-}1}$, respectively. To construct an α2 subunit expression vector, portions of partial α2 subunit cDNAs were ligated with pIBI24 (Stratagene, La Jolla, Calif.) to create HBCaCHα2. The 3600 bp EcoRI fragment of HBCaCHα2, which contained the full-length α2 subunit cDNA, was then subcloned into pCDNA1 to yield pHBCaCHα2A. Similarly, a mammalian expression vector for use in recombinant expression of a human neuronal calcium channel β subunit was constructed by ligating portions of the β subunit cDNA with pCDNA1. The resulting vector, pHBCaCHβ$_{2b}$RBS(A), contained a cDNA encoding a full-length β subunit in which approximately 800 bp of 5' untranslated sequence was replaced with an efficient ribosome binding site (ACCACC).

B. Transfection of HEK 293 Cells

HEK 293 cells were transfected using the calcium phosphate transfection procedure [*Current Protocols in Molecular Biology*, Vol. 1, Wiley Inter-Science, Supplement 14, Unit 9.1.1-9.1.9 (1990)]. Plates (10 cm), each containing one-to-two million HEK 293 cells, were transfected with 1 ml of DNA/calcium phosphate precipitate containing 5 μg pVDCCIII(A) or 8 μg pCDNAα$_{1B\text{-}1}$, 5 μg pHBCaCHα2A, and 5 μg pHBCaCHβ$_{2b}$RBS(A) as well as 5 μg pCMVBgal and 1 μg pSV2neo (as a selectable marker). After 10–20 days of growth in media containing 500 μg G418, colonies had formed and were isolated using cloning cylinders.

EXAMPLE 3

This example demonstrates the ability of the automated assay to detect agonist and/or antagonist activity of compounds which affect muscarinic acetylcholine receptors, nicotinic acetylcholine receptors or calcium channels.

A. Automated Assay for Measuring the Presence and Response of Muscarinic Receptors Stably transfected muscarinic receptor-expressing LM124-3 cells were plated into 16 wells (2 columns of 8 rows) of a 96-well plastic plate (Costar, Cambridge, Mass.; Catalog No. 3596) at a density of about 250,000 cells per well and incubated overnight at 37° C. in a humidified chamber with 10% $CO_2$. Following the incubation, the medium was removed and the plate was washed with 200 microliters per well of HEPES-buffered saline (120 mM NaCl, 5 mM KCl, 0.62 mM $MgSO_4$, 1.8 mM $CaCl_2$, 6 mM glucose, 10 mM HEPES, pH 7.4). The cells were then loaded with the calcium-sensitive indicator Fluo-3 (Molecular Probes, Inc., Eugene, Oreg.; Catalog No. F1242). Fluo-3 was prepared by reconstituting a 50 μg vial to 1 mM by adding 44 microliters dimethylsulfoxide (DMSO). Pluronic F-127; which detergent is used to render the cells permeable to Fluo-3, is included with the Fluo-3 dye reagent. Pluronic F-127 was prepared by dissolving 322 mg of pluronic F-127 in 966 μl of DMSO and heating to 45° C. until dissolved to yield a 25% stock solution. 18 μl of the 25% pluronic F-127 was added to the reconstituted Fluo-3.

A 20 μM solution of reconstituted Fluo-3 dye and 0.2% pluronic F-127 was made by adding the contents of the soluble Fluo-3 (including the pluronic F-127 mixture) to 2.2 ml of HEPES-buffered saline (HBS).

25 μl of the 20 μM Fluo-3/DMSO/pluronic F-127 solution was added to each well of the plates and incubation was carried out for three hours at room temperature in a humidified chamber.

At the end of the three hour incubation, the dye was removed using a multi-channel pipetter and each well was washed with 180 μl of HBS. The fluorometer, Fluoroskan II (ICN Biomedicals, Inc., Horsham, Pa.), as provided by the manufacturer, is capable of reading the 16 wells (columns 1+2) in approximately a 15 second time period not including the lag period for start-up. Because it was desired to read each reaction between about 30 and 50 seconds after the reaction was started with addition of the agonist (carbachol), the plate was placed in the Fluoroskan II unit such that the first well would be read at about 30 seconds after addition of the agonist. The assay was conducted using quadruplicate wells for each treatment. Each set of four wells received 180 μl of HBS. In one set of quadruplicate wells, no muscarinic receptor antagonist was added. In the second set of four wells, the HBS was supplemented with 1 μM atropine; in the third set of four wells, the HBS was supplemented with 10 μM pirenzepine; and in the fourth set of replicate wells the HBS was supplemented with 1 μM scopolamine. The plate was incubated at room temperature for three minutes to allow the antagonist compounds to equilibrate with the muscarinic receptors. The pre-reagent fluorescence was measured. Then, 20 μl of 10 mM carbachol (CCh) was added so that the final concentration of carbachol in each well was 1 mM (alternatively, wells may receive 80 μl of HBS and 20 μl of 5 mM CCh). The 20 μl aliquots of carbachol were added with a multiple pipetter and the plate was inserted in the Fluoroskan approximately 20 seconds after addition of the agonist. The plate was read at a rate of about 1 well per second thereafter such that each of the 16 wells were read between 30 and 50 seconds after the reaction was started. The treatments and results were as follows:

| Treatment | Fluorescence S/N ratio[a] |
| --- | --- |
| 1 mM carbachol (CCh) | 1.6 |
| 1 μM atropine + 1 mM CCh | 1.0 |
| 10 μM pirenzepine + 1 mM CCh | 1.0 |
| 1 μM scopolamine + 1 mM CCh | 1.0 |

[a]Calculated according to Equation 2 hereinabove.

The results indicate that carbachol induces activation of muscarinic receptors in stably transfected LM124-3 cells which results in an increase in calcium ions in the cytoplasm which is detectable by an increase in fluorescence of the cells. The results also show that the muscarinic receptor antagonists atropine, pirenzepine and scopolamine at the concentrations tested, inhibit muscarinic receptor function. In the absence of muscarinic receptor activation, the fluorescence signal remains substantially at pre-reagent levels.

A positive control cell line which may be used to measure muscarinic receptor activity (HM1 and/or HM2 forms) is the human neuroblastoma cell line SHSY5Y.

Two columns of a microtiter plate were seeded with SHSY5Y cells at a concentration of 250,000 cells per well and treated essentially as the LM124-3 cells with respect to dye-loading. The measurement of muscarinic receptor function, however, was altered. From the previous experiment it was concluded that the reaction kinetics play a very important role and that more data points were needed soon after drug (e.g., carbachol) addition. Therefore, two major modifications of the assay design were introduced (see Example 4). First, a computer program was developed to take multiple readings from a well.

Second, after software design, testing and incorporation of a liquid handling device (Digiflex) was conducted. Pharmacological analysis was then performed. The wells were measured 5 times before drug addition, then drug was automatically added followed by a 2 second delay, then readings were taken for the next 2 minutes. Typically the fluorescence peaked between 5–15 seconds for muscarinic acetylcholine receptors (MAChRs). The peak fluorescence signal-to-noise ratio was determined by dividing the fluorescence signal after drug addition (in the absence of antagonist) by the fluorescence signal before drug addition.

The results were as follows:

| Treatment | Fluorescence S/N ratio[a] |
|---|---|
| >1 mM carbachol (CCh) | 3.3 |
| 1 μM atropine + 1 mM CCh | 1.0 |
| 10 μM pirenzepine + 1 mM CCh | 1.0 |
| 1 μM scopolamine + 1 mM CCh | 1.0 |

[a]Calculated according to Equation 2 hereinabove.

The results indicate that carbachol induces an increase in intracellular calcium in SHSY5Y cells which is detectable by an increase in fluorescence of the fluorescent dye, Fluo-3. The muscarinic receptors of the SHSY5Y cells may be inhibited by treatment with a muscarinic receptor antagonist such as atropine, pirenzepine or scopolamine. Thus, SHSY5Y cells may serve as assay cells in fluorescence-based assays designed to detect compounds which affect functional muscarinic receptors or as a positive control in the assay.

B. Automated Assay for Measuring the Presence and Response of Nicotinic Receptors The automated assay was used to measure increases in intracellular calcium levels in the IMR32 cell line, a human neuroblastoma cell line which expresses nicotinic acetylcholine receptors (NAChR) (Sher, et al., *J. Neurochem.* 50, pp. 1708–1713 (1988)). The cells were plated and loaded with the fluorescent dye Fluo-3 and the assays were carried out substantially as described in the modified method of Example 3A except that the nicotinic receptors of the cells were activated. Each of the wells contained 180 μl of HBS alone or supplemented with one of the following nicotinic receptor inhibitors: 1 mM D-tubocurarine (DTC; Sigma) hexamethonium (Sigma), mecamylamine (Sigma) and atropine (Sigma). The assays were carried out in triplicate wells after the addition to each well of 20 μl of 2.0 mM nicotine. The results were as follows:

| Treatment | Fluorescence S/N ratio[a] |
|---|---|
| 200 μM nicotine | 2.3 |
| 1 mM DTC + 200 μM nicotine | 1.0 |
| 1 mM hexamethonium + 200 μM nicotine | 1.0 |
| 10 mM mecamylamine + 200 μM nicotine | 1.0 |
| 1 mM atropine + 200 μM nicotine | 1.0 |

[a]Calculated according to Equation 2 hereinabove.

The results indicate that nicotine induces activation of the nicotinic acetylcholine receptors in IMR32 cells, which can be inhibited by pretreatment of the cells with a nicotinic receptor antagonist, and that the activation of nicotinic receptors may be studied using the automated fluorescence assays of the invention.

C. Automated Assay for Measuring the Presence and Response of Calcium Channels

1. Assays of IMR32 and SHSY5Y Cells

The protocol used to evaluate the calcium flux through calcium channels in the cells expressing voltage-dependent calcium channels was similar to that described for assaying nicotinic acetylcholine receptors in Example 4B except that the reaction was initiated by depolarizing the cells with KCl (to 50 mM) and fluorescence measurements were recorded as described in Example 4. SHSY5Y cells, induced for six days with 10 μM retinoic acid (Sigma), and IMR32 cells, induced for ten days with 1 mM dibutyryl cAMP (dbcAMP) and 2.5 μM bromodeoxyuridine (BrdU) (both from Boehringer-Mannheim, Indianapolis, Ind.) were treated with various calcium channel interactive drugs before KCl depolarization and measurement of fluorescence. Induction of SHSY5Y cells and IMR32 cells reportedly causes increased expression of functional endogenous calcium channels. The calcium channel agonist, Bay K 8644, which binds to open calcium channels and prolongs their open state, was obtained from Research Biochemicals, Inc., Natick, Mass. The calcium channel antagonists are verapamil (Sigma) and, the inorganic calcium blocker, cadmium (Sigma). The treatments were as follows:

| | Fluorescence Signal to Noise Ratio[a] | |
|---|---|---|
| Treatment | SHSY5Y | IMR32 |
| 50 mM KCl | 1.9 | 2.3 |
| 50 mM KCl and 1 μM BayK 8644 | 2.7 | 2.5 |
| 50 mM KCl and 25 μM verapamil | 1.2 | 1.7 |
| 50 mM KCl and 200 μM cadmium | 1.0 | 1.0 |

[a]Calculated according to Equation 2 hereinabove.

The results indicate that KCl induces calcium influx which increases the intracellular concentration of calcium in SHSY5Y and IMR32 cells. The results also show that the calcium influx can be potentiated with Bay K 8644 and inhibited by calcium channel antagonists or blockers. Thus, SHSY5Y and IMR32 cells may be used in fluorescence-based automated assays (e.g., as positive control cells) designed to detect functional calcium channel activity.

2. Assays of Recombinant HEK 293 Cells

HEK 293 cells that had been transfected with cDNAs encoding human neuronal calcium channel α1, α2 and β subunits (see Example 2), and selected for stable expression were screened using the automated fluorescence-based assay to identify transfectant cell lines that were the most highly responsive to KCl depolarization. The assays were conducted using the fully automated version of the assay, as described for analysis of calcium channels in positive control IMR32 and SHSY5Y cells. Fluorescence was measured prior to addition of KCl to the cells to record pre-reagent fluorescence, i.e., noise, fluorescence. Signal fluorescence is the maximal fluorescence recorded after addition of KCl to the cells. The results of the screening- of cells that were transfected with DNA encoding the human neuronal $\alpha_{1D}$, $\alpha_2$ and β subunits were as follows:

| CELL LINE | S/N[a] |
|---|---|
| 1old α1D | 1.16 ± 0.01 (4) |
| 4old α1D | 1.10 ± 0.05 (4) |
| 8old α1D | 1.33 ± 0.13 (4) |
| 10old α1D | 1.04 ± 0.01 (4) |
| 11old α1D | 1.01 ± 0.01 (4) |
| 12old α1D | 1.38 ± 0.17 (20) |
| 13old α1D | 1.88 ± 0.06 (12) |
| HEK 293 (untransfected) | 1.03 ± .03 (3) |

[a]S/N ± standard deviation; numbers in parentheses represent the number of assays These results indicated that cell line 13old expressed the highest level of functional calcium channels. Therefore, this cell line was used in additional automated fluorescence-based assays designed to investigate the pharmacology of the calcium channels expressed in the cells.

Cell line 13old was tested for dose-dependent effects of Bay K 8644 (a dihydropyridine (DHP) which is an agonist of DHP-sensitive calcium channels), and three calcium channel antagonists, verapamil, cadmium and omega-CgTx, on KCl-induced fluorescence increases in the cells. The automated assays were performed as described for analysis of calcium channel activity of IMR32 and SHSY5Y cells. For each dose-dependence assay, different wells of the microtiter plate received different concentrations of the agonist or antagonist, the background fluorescence was measured, and KCl was added to a predetermined well via the DigiFlex System. Repeated fluorescence measurements were made before and after KCl addition and the values were recorded. A total of five fluorescence readings were taken before KCl addition. The instrument then moves the plate to the reagent-adding position and 20 μl of 0.5 M KCl was added to the well (50 mM KCl, final concentration) by the Digiflex pipetter. The plate was then automatically repositioned at the fluorescence measuring position (a delay of two seconds was measured between reagent addition and the first fluorescence measurement after reagent addition) and 125 fluorescence measurements were taken and values were recorded. Following each assay of a well, another well was assayed until all of the predetermined wells had been assayed. The maximum fluorescence measured for each compound tested and the compound concentration that yielded the maximum fluorescence were noted.

Dose-response curves were generated from the fluorescence data. In constructing these curves, the fluorescence value recorded in the presence of each concentration of compound was plotted as the percent maximum fluorescence vs. concentration. It was possible to estimate $EC_{50}$ and $IC_{50}$ values from these curves.

Increasing concentrations of Bay K 8644 potentiated the fluorescence response to KCl in 13old cells, which was maximal at 100 nM. The $EC_{50}$ for the potentiation of fluorescence response by Bay K 8644 was estimated at 4.4 nM. Verapamil inhibited the fluorescence response with an $IC_{50}$ of approximately 6.0 μM and cadmium with an $IC_{50}$ of 3.0 μM. The antagonist omega-CgTx did not completely inhibit the KCl-induced fluorescence increase in 13old cells.

HEK 293 cells that were transfected with DNA encoding the human neuronal calcium channel $\alpha_{1B}$, $\alpha_2$, and β subunits were also screened for functional calcium channels using the automated fluorescence-based assay. In these assays, the cells were contained in a solution containing $CaCl_2$ (~1.8 mM), NaCl (~125 mM), HEPES (~20 mM), glucose (~6 mM) and $MgCl_2$ (~0.6 mM) during loading with Fluo-3. Prior to initiation of the assay (i.e., addition of KCl to the wells), valinomycin (~10 μM) was added to the wells in an effort to lower the resting potential of the cell membrane. To activate the calcium channels, a 5× solution containing KCl (~350 mM) and calcium (~2 mM) was added to the wells via the automatic pipetter. In some assays, the media contained in the wells after dye loading can be changed by introducing a solution containing 1-methyl-D-glucamine (~140 mM) and no added calcium. After incubation of the cells in this media for ~15 minutes, calcium is added to the wells to a final concentration of 2 mM and the cells are treated with valinomycin (~10 μM) prior to initiating the assay.

EXAMPLE 4

This Example demonstrates the automation of the fluorescent dye-based assays of the invention resulting in increased efficiency in conducting the assays and increased reliability of the results.

The results of the assays of LM124-3 cells presented in Example 3A were obtained by measuring the fluorescence once per well, 20–30 seconds after addition of reagent (i.e., carbachol). Significant variations in the relative amount of fluorescence measured and the calculated signal-to-noise ratios were observed due to the kinetics of the fluorescence reaction. The software controlling the Fluoroskan II was rewritten so as to direct a well of the plate to remain under the excitation/emission head for an extended period of time in order to allow the fluorescence from the well to be measured and recorded repetitively which improved the reliability of the results (i.e., decreased the standard deviation). Using the new program, allowing continuous reading from individual wells, the change in fluorescence over time (i.e., kinetics) could be studied and it was possible to identify a maximal fluorescence response. However, this undesirably limited the number of assays which could be conducted per hour because reagent had to be added to the one well at a time immediately before that well was read in the fluorometer. The average time between addition of reagent and the first reading was reduced from about 10 seconds to about 6 seconds, but only a single well could be read at one time.

To accomplish rapid drug addition and nearly immediate reading of the fluorescence response, the Fluoroskan II was further modified by fitting a Digiflex TP automatic pipetter and developing a software program to accomplish precise computer control over both the Fluoroskan II and the Digiflex TP. By integrating the combination of the Fluoroskan II and the Digiflex TP and using a microcomputer to control the commands to the fluorometer and automatic pipetter, the delay time between reagent addition and fluorescence reading was reduced from about 6 seconds to about 2 seconds. Moreover, both greater reproducibility and higher signal-to-noise ratios have been achieved as compared to manual addition of reagent since the computer repeats the process precisely time after time. And, extremely advantageously, a plurality of assays may be conducted seriatim, without manual intervention. The results of the fluorescent dye-based assays for muscarinic acetylcholine receptors carried out by manual addition of reagent followed by a single fluorescence measurement (I), manual addition of reagent followed by substantially continuous fluorescence measurements (94 readings per minute) (II) and automatic injection of reagent followed by substantially continuous fluorescence measurements (III) are shown in the table below:

Summary of Carbachol Induction Data from the Development of the Fluorescent Dye-Based Assay for Muscarinic Acetylcholine Receptors

| Assay Development Stage | | Cell Line | |
|---|---|---|---|
| | | LM124-3 | SHSY5Y |
| I. | Manual addition of CCh, 30 second delay before single fluorescence measurement | $\overline{S:N}$ = 1.55<br>S.D. = 0.40<br>(n = 68) | N.D. |
| II. | Manual addition of CCh, 6 second delay before multiple fluorescence measurements | $\overline{S:N}$ = 2.0<br>S.D = 0.3<br>(n = 34) | $\overline{S.N.}$ = 3.3<br>S.D. = 0.4<br>(n = 38) |
| III. | Automatic injection of CCh, 2 second delay before multiple fluorescence measurements | $\overline{S:N}$ = 2.12<br>S.D. = 0.16<br>(n = 5) | $\overline{S:N}$ = 3.62<br>S.D. = 0.16<br>(n = 11) |

$\overline{S:N}$ = Average CCh-induced signal-to-noise ratio = $\dfrac{\text{PeakorMaximalFluorescenceSignal+CCh}}{\text{Fluorescence Signal} - \text{CCh}}$
N.D. = Not Determined
S.D. = Standard Deviation
n = number of determinations Thus, with automatic delivery of reagent followed by multiple fluorescence measurements, reliability of the fluorescent dye-based assay as well as the number of assays that can be performed per day are advantageously increased.

While the invention has been described herein with some specificity, the ordinarily skilled in the art will recognize numerous variations and modifications, in what is described, that are within the spirit of the invention. Such variations and modifications are within the scope of the invention as described and claimed herein.

What is claimed is:

1. An automated method for detecting or measuring the activity of ion channels and/or receptors of a cell, comprising:

(a) introducing a divided culture vessel having an array of individual compartments into an apparatus, wherein:
at least two compartments contain cells to be assayed for the activity of ion channels and/or receptors;
the ion channels and/or receptors when activated, directly or indirectly, cause a change in the concentration of a predetermined ion in the cytoplasm of the cells;
the cytoplasm of the cells comprise an amount of an ion-sensitive fluorescent indicator sufficient to detect a change in the concentration of the predetermined ion; and
the apparatus delivers reagent solution to one or more compartments of the divided culture vessel and detects or measures an attribute of the contents of each compartment;

(b) automatically delivering to one or more of the compartments an amount of a known ion channel- or receptor-activating compound that is effective to activate the ion channel or receptor;

(c) within a predetermined time that is less than the time for any induced change in ion concentration to reach a maximum, automatically detecting and measuring, in one or more of the individual compartments for a predetermined amount of time, a change in ion concentration by measuring fluorescence emitted by the ion-sensitive indicator in response to an excitation wavelength, whereby the activity of ion channels and/or receptors of a cell is detected or measured.

2. The method of claim 1 wherein at least two of the individual compartments contain cells being assayed for the presence of ion channels and/or receptors, and steps (b) and (c) are repeated at least once.

3. The method of claim 1 further comprising (d) repeating steps (b) and (c) in turn for each of the remaining compartments that contain cells until all the individual compartments containing the cells have been assayed.

4. The method of claim 1, wherein the compound is added to more than one compartment at a time.

5. The method of claim 4, wherein detecting and measuring of fluorescence is effected in more than one compartment at a time.

6. The method of claim 1, wherein during measurement, the compartment on which measurement is effected is sufficiently aligned with measuring and detecting means in the apparatus to permit measurement or detection.

7. The method of claim 6, wherein measurement is effected on more than one compartment at a time and more than one compartment is sufficiently aligned with measuring and detecting means in the apparatus to permit measurement or detection.

8. The method of claim 1, wherein measurement is effected in more than one compartment at a time using a charge coupled device (CCD) or a photodiode array in response to computer control.

9. An automated drug screening assay for identifying compounds that modulate activity of ion channels and/or receptors of a cell, comprising (a) introducing a divided culture vessel having an array of individual compartments into an apparatus, wherein:
at least two compartments contain cells to be assayed comprising ion channels and/or receptors that when activated, directly or indirectly, cause a detectable change in the concentration of a predetermined ion in the cytoplasm of the cells;
the cytoplasm of the cells comprises an amount of an ion-sensitive fluorescent indicator sufficient to detect a change in the concentration of the predetermined ion; and
the apparatus delivers reagent solution to one or more compartments of the divided culture vessel and detects and measures an attribute of the contents of the individual compartments;

(b) automatically delivering to one or more predetermined compartments an aliquot of a solution comprising either or both of (i) an amount of a known ion channel- or receptor-activating compound that is effective to activate the ion channel or receptor, and (ii) a test compound of unknown ion channel or receptor activity; and (c) within a predetermined time that is less than an amount of time for any induced ion flux to reach a maximum, detecting and measuring, in one or more of the individual compartments for a predetermined amount of time, the induced ion flux by detecting or measuring fluorescence emitted by the ion-sensitive indicator in response to an excitation wavelength, whereby compounds that modulate activity of ion channels and/or receptors of a cell are identified.

10. The assay of claim 9, wherein at least two of the individual compartments contain cells to be delivered a compound and steps (b) and (c) are repeated at least once.

11. The assay of claim 9, further comprising (d) repeating steps (b) and (c) in turn for each compartment containing cells until all the compartments containing the cells have been assayed.

12. The assay of claim 11, wherein:
a compound is tested for its ability to activate ion channels or receptors;
the aliquot delivered comprises an amount of the test compound; and wherein,
after step (d), fluorescence intensity is determined in each of the compartments containing the cells to which the test compound is added, relative to the fluorescence intensity produced by at least one compartment containing substantially identical cells that does not receive the known activating compound or test compound.

13. The assay of claim 9, wherein at least one of the compartments containing the cells also contains the test compound and the known activator of the receptor or ion channel is delivered by the apparatus.

14. The assay of claim 13, wherein the cells have voltage-dependent calcium channels and ligand-gated ion channels and the test compound inhibits activation of the ligand-gated ion channels.

15. The assay of claim 9, wherein in step (b) the known activator of the receptor or ion channel is delivered by the apparatus along with the test compound to at least one of the compartments containing the cells.

16. The assay of claim 9, wherein in step (b) a test compound and a known activator of the receptor or ion channel are delivered successively to at least one of the compartments containing the cells.

17. The assay of claim 9, wherein in step (b) only the test compound is delivered by the apparatus to at least one of the compartments containing the cells.

18. The assay of claim 9, wherein:
a compound is tested for its ability to inhibit or potentiate ion channels or receptors; and
wherein: (i) at least a portion of the compartments containing the cells further comprise the test compound; (ii) each of the aliquots delivered comprise an effective amount of a known activating compound; and (iii) after step (d), the intensity of fluorescence in each of the individual compartments containing the cells comprising the test compound is determined, relative to the intensity of fluorescence in at least one compartment containing the cells and treated substantially identically, except in the absence of the test compound.

19. The assay of claim 9, wherein the ion channels or receptors flux the ion when activated and the cells are bathed in a solution comprising a concentration of the ions which is sufficient to cause a detectable increase in the level of the ions in the cytoplasm when the ion channels or receptors are activated.

20. The assay of claim 19, wherein the cells comprise voltage-dependent calcium channels and the solution bathing the cells comprises a concentration of calcium ions which is sufficient to cause a detectable increase in the level of calcium ions in the cytoplasm of the cells when the calcium channels are activated by membrane depolarization.

21. The assay of claim 20, wherein the solution delivered in step (b)(i) comprises a membrane-depolarizing amount of potassium ions.

22. The assay of claim 19, wherein the cells have ligand-gated ion channels.

23. The assay of claim 22, wherein the ligand-gated ion channel is selected from the group consisting of nicotinic acetylcholine receptors and kainate/α-amino-3-hydroxy-5-methyl-isoxazole-4-propionic acid (AMPA) receptors.

24. The assay of claim 9, wherein:
   at least one of the compartments contains non-expressing cells that do not express the cell surface receptor or ion channel but to which test compound has been added or that contain said non-expressing cells to which the test compound has not been added; and
   the intensity of fluorescence in each of the compartments containing the cells comprising a test compound is determined, relative to the intensity of fluorescence in at least one compartment that is treated substantially identically but that contains said non-expressing cells to which test compound has been added or said non-expressing cells to which test compound has not been added.

25. The assay of claim 9, wherein the cells are recombinant cells that express heterologous calcium channels.

26. The assay of claim 25, wherein the recombinant cells are transfected human embryonic kidney cells.

27. The assay of claim 9, wherein the cells have voltage-dependent calcium channels and ligand-gated ion channels, wherein the solution delivered in step (b) comprises an amount of a known activator of the ligand-gated ion channel or a test compound, and wherein activation of the ligand-gated ion channel depolarizes the cell membrane, whereby voltage-dependent calcium channels open.

28. The assay of claim 9, wherein the cells have voltage-dependent calcium channels and ligand-gated ion channels, wherein the solution delivered in step (b) comprises an amount of a known activator of the ligand-gated ion channel and a test compound and the test compound inhibits activation of the ligand-gated ion channels.

29. The assay of claim 9, wherein:
   the cells comprise a G-protein-coupled receptor; the solution delivered in step (b) comprises a known activator of the G-protein-coupled receptor or a test compound; and
   activation of the receptor causes an increase in the level of cytoplasmic calcium ions.

30. The assay of claim 29, wherein the G-protein-coupled receptor is selected from the group consisting of metabotropic excitatory amino acid (EAA) receptors and muscarinic acetylcholine receptors.

31. The assay of claim 9, wherein the fluorescent indicator is 9-(4-bis(carboxymethyl)amino-3-(2-(2-bis-(carboxymethyl)amino-5-methylphenoxy)ethoxy)phenyl)-2,7-dichloro-6-hydroxy-3 H-xanthen-3-one (fluo-3).

32. The automated drug screening assay of claim 9, wherein in step (b) solution is delivered to one predetermined compartment followed by detection and measurement for a predetermined amount of time of fluorescence in that compartment.

33. The assay of claim 32, wherein steps (b) and (c) are repeated in turn in all of the compartments containing the cells.

34. The assay of claim 9, wherein the compound is added to more than one compartment at a time.

35. The assay of claim 34, wherein detecting and measuring of fluorescence is effected in more than one compartment at a time.

36. The assay of claim 9, wherein during measurement, the compartment on which measurement is effected is sufficiently aligned with measuring and detecting means in the apparatus to permit measurement or detection.

37. The assay of claim 36, wherein measurement is effected on more than one compartment at a time and more than one compartment is sufficiently aligned with measuring and detecting means in the apparatus to permit measurement or detection.

38. The method of claim 9, wherein measurement is effected in more than one compartment at a time using a charge coupled device (CCD) or a photodiode array in response to computer control.

39. An automated method for detecting or measuring an occurrence of a cellular event that directly or indirectly induces a change in intensity of an optical attribute of an indicator moiety in response to the cellular event, comprising:
   (a) introducing a divided culture vessel having an array of individual compartments into an apparatus, wherein:
      at least one compartment contains cells that, when contacted with a compound that causes the cellular event to occur, undergo the cellular event;
      the cytoplasm of the cells comprises an amount of the indicator moiety sufficient to exhibit a detectable change in the intensity of the optical attribute upon occurrence of the event; and
      the apparatus has delivery means to deliver reagent solution to one or more compartments of the divided culture vessel and means to detect and measure at least one optical attribute of the contents of the compartments;
   (b) automatically delivering to one or more predetermined compartments, an aliquot of a solution comprising an amount of a compound that causes the cellular event to occur thereby allowing a detectable increase in the intensity of the optical attribute in the compartment containing the cells to be measured, wherein the delivery means and predetermined compartments are aligned; and
   (c) within a predetermined time period that is less than the time for the cellular event indicated by the change in the intensity of the optical attribute to reach its peak, detecting and measuring in one or more of the predetermined compartments for a predetermined amount of time the intensity of the optical attribute emitted by the cells, wherein the detecting and measuring means and predetermined compartments are aligned, and whereby the occurrence of a cellular event is detected or measured.

40. The method of claim 39, wherein:
   the cells express amino acid transporter function;
   the cellular event is amino acid transport; and the indicator moiety is an amino acid-fluorescent indicator conjugate.

41. The method of claim 39, wherein the cellular event is a change in an intracellular concentration of one or more cyclic nucleotides.

42. The method of claim 39, wherein the compound is added to more than one compartment at a time.

43. The method of claim 42, wherein detecting and measuring of the optical attribute is effected in more than one compartment at a time.

44. The method of claim 39, wherein during measurement, the compartment on which measurement is effected is sufficiently aligned with measuring and detecting means in the apparatus to permit measurement or detection.

45. The method of claim 44, wherein measurement is effected on more than one compartment at a time and more than one compartment is sufficiently aligned with measuring and detecting means in the apparatus to permit measurement or detection.

46. The method of claim 39, wherein the cellular event is cell injury or cell death and the indicator moiety is a pH sensitive fluorescent indicator.

47. The method of claim 39, wherein the cellular event is modulation of the activity of an ion-channel or receptor and the indicator moiety is a ion-sensitive indicator.

48. The method of claim 39, wherein the cellular event is a change in the concentration of one or more cyclic nucleotides and the indicator moiety is cyclic AMP-dependent-protein kinase indicator conjugate.

49. An automated method for identifying compounds that induce the occurrence of a cellular event that results in a change in the intensity of an optical attribute of an indicator moiety in response to the cellular event, the method comprising:
   (a) introducing a divided culture vessel having an array of individual compartments into an apparatus, wherein:
      (i) at least one compartment contains cells that when contacted with a compound that causes the cellular event to occur, undergo the cellular event;
      (ii) the cytoplasm of the cells comprises an amount of an indicator moiety sufficient to exhibit a detectable change in the intensity of the optical attribute upon occurrence of the event; and
      (iii) the apparatus has delivery means to deliver reagent solution to one or more compartments of the divided culture vessel, and detecting and measuring means to detect and measure at least one attribute of the contents of the compartments;
   (b) automatically delivering to one or more predetermined compartments an aliquot of a solution comprising either or both of (i) an amount of a known compound that is effective to induce the cellular event; and (ii) a test compound of unknown activity; and
   (c) within a predetermined time period that is less than the time for the cellular event indicated by the change in the intensity of the optical attribute to reach a maximum, detecting and measuring in one or more of the predetermined compartments, for a predetermined amount of time the level of the optical attribute emitted by the cells, wherein the detecting and measuring means and the predetermined compartments are aligned, whereby a compound that induces the occurrence of a cellular event is identified.

50. The method of claim 49, wherein the compound is added to more than one compartment at a time.

51. The method of claim 50, wherein detecting and measuring of the optical attribute is effected in more than one compartment at a time.

52. The method of claim 49, wherein during measurement, the compartment on which measurement is effected is sufficiently aligned with measuring and detecting means in the apparatus to permit measurement or detection.

53. The method of claim 49, wherein measurement is effected on more than one compartment at a time and more than one compartment is sufficiently aligned with measuring and detecting means in the apparatus to permit measurement or detection.

54. The method of claim 53, wherein measurement is effected in more than one compartment at a time using a charge coupled device (CCD) or a photodiode array in response to computer control.

55. The method of claim 49, wherein measurement is effected in more than one compartment at a time using a charge coupled device (CCD) or a photodiode array in response to computer control.

56. The method of claim 49, wherein the test compound and unknown compound are added simultaneously.

57. The method of claim 49, wherein the test compound and unknown compound are added serially.

58. A method for automatically measuring an optical attribute indicative of occurrence of a transient reaction in a computer-controlled measurement apparatus, the method comprising:
   (a) introducing an ion-sensitive indicator into cells in a plurality of wells of a multi-well plate containing samples to be measured;
   (b) identifying at least one predetermined well of a plurality of wells of a multi-well plate containing samples to be measured;
   (c) aligning the predetermined well(s) by the apparatus with a predetermined position;
   (d) adding reagent by the apparatus to the predetermined well(s) at the predetermined position(s), wherein the reagent induces directly or indirectly the transient reaction;
   (e) measuring the optical attribute of the predetermined well(s) while aligned with the position(s), wherein commencement of measurement occurs within a predetermined time period that is less than the time required for the reaction to reach its peak response and measurement is effected for a predetermined amount of time, whereby the optical attribute indicative of a transient reaction is automatically measured in the computer-controlled apparatus.

59. The method of claim 58, wherein the reagent is added to more than one compartment at a time.

60. The method of claim 59, wherein measuring is effected in more than one compartment at a time.

61. The method of claim 58, wherein during measurement, the compartment on which measurement is effected is sufficiently aligned with measuring and detecting means in the apparatus to permit measurement or detection.

62. The method of claim 61, wherein measurement is effected on more than one compartment at a time and more than one compartment is sufficiently aligned with measuring and detecting means in the apparatus to permit measurement or detection.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

CCCCAGCCCC ACCTTGAATT CATGAACACT TCAGCC    36

(2) INFORMATION FOR SEQ ID NO:2:

(i) SEQUENCE CHARACTERISTICS:

```
            (A) LENGTH: 18 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

CACCTTGAAT TCATGAAC                                                    18

(2) INFORMATION FOR SEQ ID NO:3:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

CTCCCGCCAA TGCTGAGAAT TCTATCTCCT GCATCCC                               37

(2) INFORMATION FOR SEQ ID NO:4:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

CTGAGAATTC TATCTCC                                                     17
```